(12) United States Patent
Guerineau et al.

(10) Patent No.: US 11,034,970 B2
(45) Date of Patent: Jun. 15, 2021

(54) **PRODUCTION OF PROTEIN FROM HAIRY ROOTS OF A *BRASSICACEAE* PLANT UTILIZING RHIZOBIUM COMPRISING ROL GENES**

(71) Applicant: UNIVERSITE DE PICARDIE JULES VERNE, Amiens (FR)

(72) Inventors: Francois Guerineau, Salouel (FR); Michele Aimee Yvonne Boitel-Conti, Amiens (FR); Jean Pierre Ele Ekouna, Amiens (FR)

(73) Assignee: UNIVERSITE DE PICARDIE JULES VERNE, Amiens (FR)

( * ) Notice: Subject to any disclaimer, the term of this patent is extended or adjusted under 35 U.S.C. 154(b) by 1 day.

(21) Appl. No.: 15/574,069

(22) PCT Filed: May 13, 2016

(86) PCT No.: PCT/FR2016/051149
§ 371 (c)(1),
(2) Date: Nov. 14, 2017

(87) PCT Pub. No.: WO2016/185122
PCT Pub. Date: Nov. 24, 2016

(65) Prior Publication Data
US 2019/0040407 A1 Feb. 7, 2019

(30) Foreign Application Priority Data
May 15, 2015 (FR) ........................ 15/01002

(51) Int. Cl.
*C12N 15/82* (2006.01)
*C12P 21/02* (2006.01)

(52) U.S. Cl.
CPC ..... *C12N 15/8257* (2013.01); *C12N 15/8202* (2013.01); *C12P 21/02* (2013.01)

(58) Field of Classification Search
None
See application file for complete search history.

(56) References Cited

U.S. PATENT DOCUMENTS

| | | | |
|---|---|---|---|
| 2004/0072317 A1* | 4/2004 | Lenee | C10L 1/02 435/198 |
| 2013/0061351 A1* | 3/2013 | Boitel-Conti | C12N 15/8221 800/294 |

FOREIGN PATENT DOCUMENTS

EP   2385130 A1   11/2011

OTHER PUBLICATIONS

Kim et al. Influence of auxins on glucosinolate biosynthesis in hairy root cultures of broccoli (*Brassica oleracea* var. italica). (2013) Asian Journal of Chemistry; vol. 25; pp. 6099-6101 (Year: 2013).*

(Continued)

*Primary Examiner* — Cathy Kingdon Worley
(74) *Attorney, Agent, or Firm* — Nixon & Vanderhye

(57) ABSTRACT

A method for producing proteins of interest from secondary root emergences which appear on the hairy roots of a plant belonging to the Brassicaceae family, in a liquid medium containing at least one auxin, comprises the use of a strain of *Rhizobium* comprising rol genes.

Figure 3:
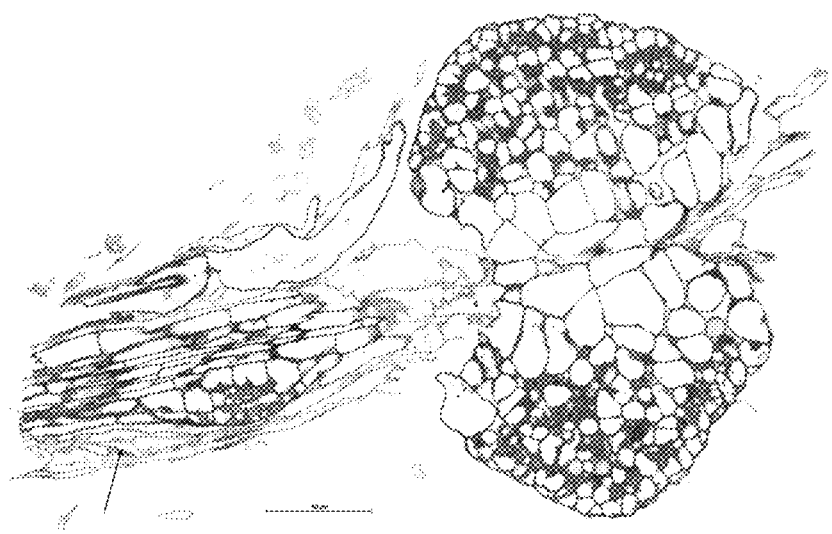

19 Claims, 7 Drawing Sheets
Specification includes a Sequence Listing.

(56) References Cited

OTHER PUBLICATIONS

Nilsson et al. Getting to the root: the role of the Agrobacterium rhizogenes rol genes in the formation of hairy roots. (1997) Physiologia Plantarum; vol. 100; pp. 463-473 (Year: 1997).*
Alexandersson et al. Plant secretome proteomics. (2013) Frontiers in Plant Science; vol. 4; pp. 1-6 (Year: 2013).*
Puddephat et al. Recovery of phenotypically normal transgenic plants of *Brassica oleracea* upon Agrobacterium rhizogenes-mediated co-transformation and selection of transformed hairy roots by GUS assay. (2001) Molecular Breeding; vol. 7; pp. 229-242 (Year: 2001).*
Quach et al. Functional analysis of water stress-responsive soybean GmNAC003 and GmNAC004 transcription factors in lateral root development in *Arabidopsis*. (2014) PLOS One; vol. 9; pp. 1-12 (Year: 2014).*
Overoorde et al. Auxin Control of Root Development (2010) Cold Spring Harbor Laboratory Press; pp. 1-16 (Year: 2010).*
Wikipedia: List of *Brassicaceae* genera. (2020) downloaded from https://en.wikipedia.org/wiki/List_of_Brassicaceae_genera on Mar. 7, 2020; pp. 1-6 (Year: 2020).*
Washida et al., "Auxins Affected Ginsenoside Production and Growth of Hairy Roots in Panax Hybrid", Medicinal & Aromatic Plants Abstract, Dec. 1, 2004, vol. 26, No. 6.
Balvanyos et al., "The effect of plant growth regulators on biomass formation and lobeline production of *Lobelia inflata* L. hairy root cultures", Plant Growth Regulation, Jul. 2001, vol. 34, pp. 339-345.
Agostini et al., "Production of peroxidases by hairy roots of *Brassica napus*", Plant Cell Tissue and Organ Culture, 1997, vol. 47, No. 2, pp. 177-182.
Zang et al., "Metabolic Engineering of Indole Glucosinolates in Chinese Cabbage Hairy Roots Expressing *Arabidopsis* CYP79B2, CYP79B3, and CYP83B1", Biotechnology and Bioprocess Engineering; 2009, vol. 14, pp. 467-473.
Gaume et al., "Rhizosecretion of recombinant proteins from plant hairy roots", Plant Cell Reports, 2003, vol. 21, pp. 1188-1193.
French Search Report, dated Mar. 15, 2016, from corresponding FR application No. 15/01002.
International Search Report, dated Jul. 25, 2016, from corresponding PCT application No. PCT/FR2016/051149.
Cardon et al., "*Brassica rapa* hairy root based expression system leads to the production of highly homogenous and reproducible profiles of recombinant human alpha-L-iduronidase," Plant Biotechnology Journal (2019) 17, pp. 505-516.
Sevon et al., "Characterization of transgenic plants derived from hairy roots of Hyoscyamus muticus," Plant Cell Reports (1997) 16: 605-611.

* cited by examiner

Figure 1
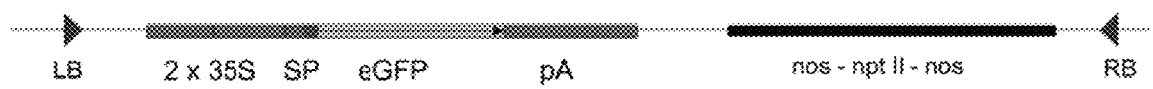
Figure 2A                    Figure 2B
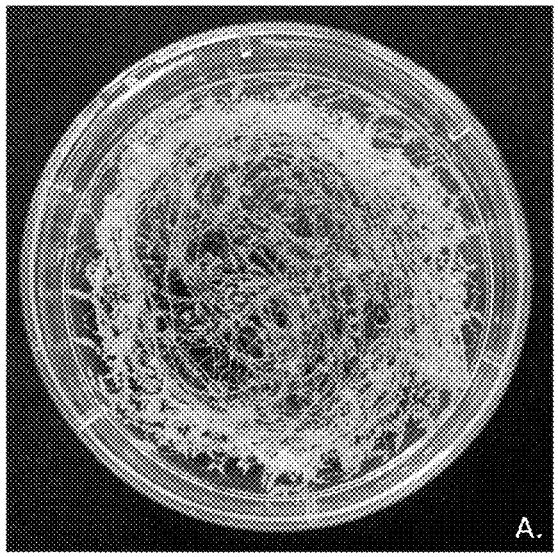  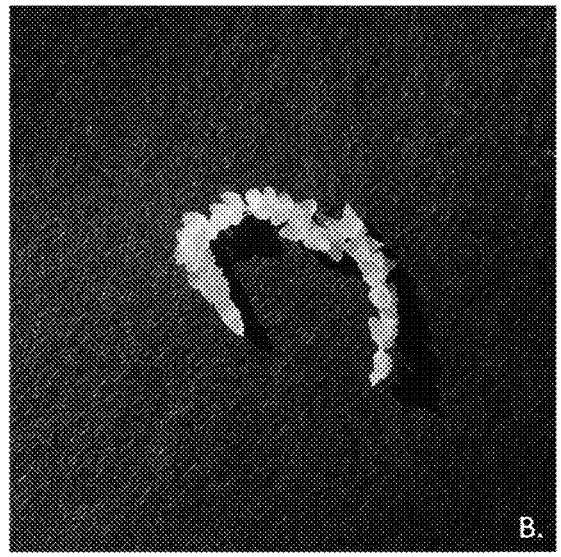

A

B

Figure 5 A
Figure 5 B
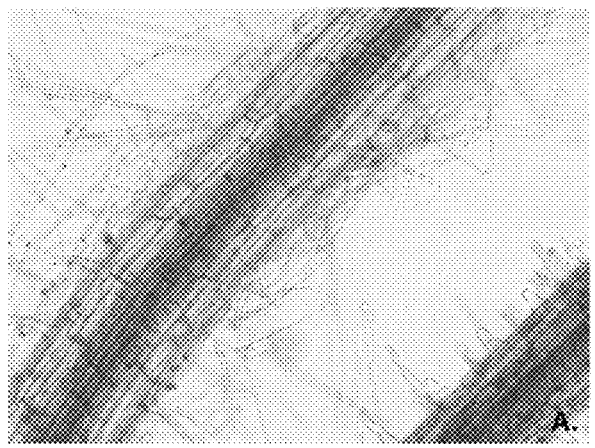
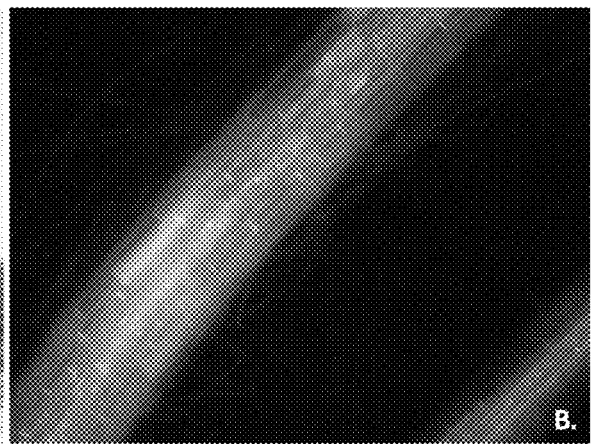
Figure 6
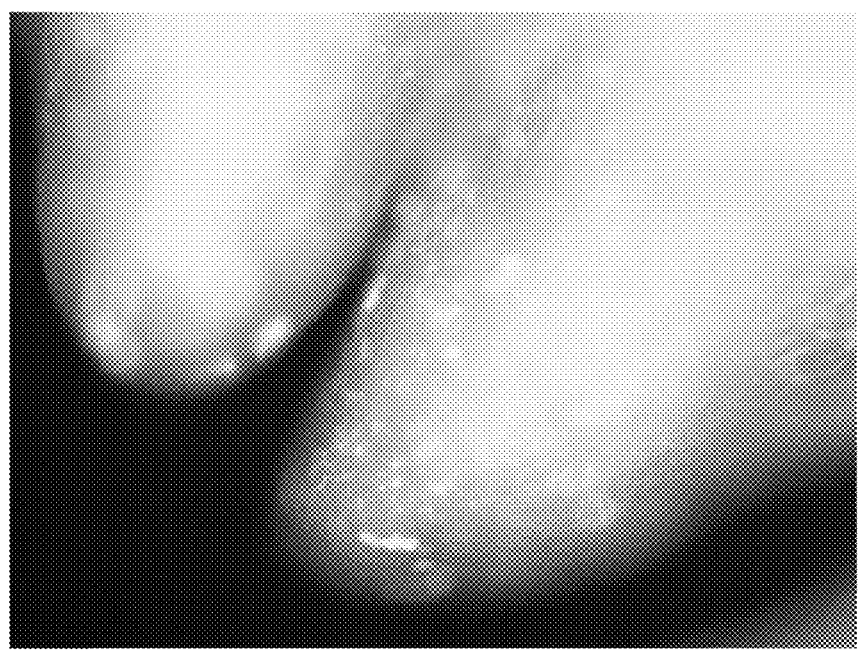

PRODUCTION OF PROTEIN FROM HAIRY ROOTS OF A *BRASSICACEAE* PLANT UTILIZING RHIZOBIUM COMPRISING ROL GENES

The invention relates to a method for producing proteins of interest from a plant structure.

The proteins are biopolymers of amino acids synthesized by all living organisms. They are involved in practically all aspects of cell life. Enzymes activate and regulate the metabolism, the structural proteins shaping the cell; the signalling proteins and the receptor proteins allow integration of the environmental changes of the cell. At present, proteins are widely used not only for industrial purposes (enzymes in detergents, food additives, bleaching agents for paper etc.) but also for medical purposes (vaccines and allergens, hormones, antibodies etc.). Before the development of molecular biology and the tools of recombinant DNA technology, the only source of proteins of interest was the organ producing them itself. For example, insulin was previously purified from pigs, while human growth hormone was extracted from human cadaver tissues. The main drawbacks of these approaches has been the limited availability of the starting material and the low content of protein of interest. Moreover, the risk of viral contamination of the proteins used for medical applications has remained high, above all when they has been extracted from human tissue. In the 1980s, recombinant DNA technology provided alternatives to these problems by allowing the overproduction of foreign proteins (recombinant proteins) in a given host organism. Animal insulin was thus the first recombinant protein with a medical application to be produced in *Escherichia coli* bacteria. At present, cultures of animal cells and of *E. coli* are the two references for the bioproduction of recombinant proteins.

However, bacteria are incapable of producing complex glycosylated proteins and the culture of animal cells is a fairly expensive process which cannot exclude the risk of contamination with a virus from the animal. Alternative bioproduction systems have thus been developed during the last two decades, including plants which are considered as safe (no viral risk), capable of producing complex proteins and inexpensive in quantity. Confining the systems of bioproduction of plant origin (in greenhouses in the case of whole plants and in bioreactors in the case of plant cells) is preferable to growing plants in open fields. Hairy roots are an example of such a confined bioproduction system, as they can easily be cultured in bioreactors and transgenic clones can be obtained in the case of any gene of interest. This particular root system is generated following the infection of the plant cell with *Rhizobium rhizogenes* which naturally transfers several bacterial genes into the genome of the plant.

*R. rhizogenes* is a pathogenic telluric bacterium of plants that is responsible for a disease called "hairy root disease". This disease is characterized by the appearance of root hairs at the point of infection by the bacterium.

The ability to induce the disease is linked to the presence in the bacterium of a plasmid of high molecular weight (approx. 300 Kb) called Ri plasmid which makes the bacteria virulent.

The root hairs result from the transfer and the expression of the genetic information borne by a fragment of the pathogenic plasmid, called T-DNA (transfer DNA) and delimited by two zones called right border (RB) and left border (LB), of the bacterium towards the nuclear genome of the plant cell.

The T-DNA of *R. rhizogenes* also comprises genes responsible for the synthesis of auxin, as well as so-called rol genes. It does not comprise any gene involved in the synthesis of cytokine. After the transfer of this T-DNA cell into a plant cell, these genes will divert the cell metabolism to force the cell of the infected plant (stem, leaf etc.) to follow a new program of development and thus to produce massive amounts of auxin. From then on, the auxin/cytokine hormone balance is shifted in favour of auxin, thus inducing significant rhizogenesis. This inducing of root formation leads to the appearance of a new root system at the site of the infection, the roots called "hairy", emerge from masses of roots exhibiting an overdevelopment of root hairs.

The strains of *R. rhizogenes* can be genetically modified in order to carry out the transfer of a gene of interest into the plant cell (encoding for example a protein of pharmaceutical interest) and thus production of the protein of interest by all of the transgenic hairy roots generated from the genetically modified cell.

It should be noted that *Agrobacterium rhizogenes* has been renamed *Rhizobium rhizogenes* following taxonomic changes to the genus *Agrobacterium* and the family of the Rhizobiaceae. *Rhizobium rhizogenes* can also be identified by the name *Agrobacterium rhizogenes*.

Numerous heterologous proteins have been produced in tissues of plants cultivated in vitro.

A heterologous protein, also called recombinant protein or protein of interest, is a protein that is not naturally synthesized by the organism that produces it. The genetic material of the cells of this organism (bacteria, cultured plant cells, cultured animal cells etc.) has been modified by genetic recombination in order to introduce into it the gene encoding the heterologous protein in order to be able to express this protein in said organism.

Kittipongpatana et al. (1998) (Production of solasodine by hairy root, callus, and cell suspension cultures of *Solanum aviculare* Forst, Plant Cell, Tissue and Organ culture 52: 133-143, 1998) have shown that cultures of hairy roots of *Solanum aviculare*, induced by *Rhizobium rhizogenes*, produced a greater quantity of solasodine, an endogenous protein of this species, than undifferentiated calluses or cultures of cells in suspension.

Hellwig et al. (2004) (Plant cell cultures for the production of recombinant proteins. Nature Biotechnology, 22: 1415-1422) address the use of hairy roots for producing recombinant proteins and increasing the yield of this production by optimizing the culture medium and conditions, and optimizing the purification of the recombinant proteins.

In application WO 2011/138233, filed by the Université de Picardie Jules Verne on 28.04.2011, the authors have developed a method for producing recombinant proteins from transgenic hairy roots, obtained by transforming plants belonging to the family of the Brassicaceae with *Rhizobium rhizogenes* and/or *A. tumefaciens*.

Xu J. et al. (2012) (Green factory: Plants as bioproduction platforms for recombinant proteins. Biotechnology Advances 30: 1171-1184), report on the different classes of recombinant proteins that can be produced by plants, different parts of plants being able to be used for producing recombinant proteins and the stable or transitory expression of the recombinant proteins.

Zhang et al. (2014) (Induction and characterization of callus from *Psammosilene tunicoides* hairy roots. Journal of Chemical and Pharmaceutical Research, 6: 1394-1399) have studied the production of a family of endogenous proteins of *Psammosilene tunicoides*, the saponins, and have shown that calluses, obtained by dedifferentiation of hairy roots cultured in an MS medium supplemented with 2,4-D auxin, were capable of producing as many saponins as non-dedifferentiated hairy roots in calluses, and a production that is four times greater than calluses obtained from other plant organs (leaves, flowers etc.).

A subject of the present invention is a method for producing protein of interest from lateral root emergences appearing on hairy roots of a plant belonging to the family of the Brassicaceae, in liquid medium containing at least one auxin, comprising the steps of:

a) transforming a plant belonging to the family of the Brassicaceae with a strain of *Rhizobium* comprising the rol genes, in order to obtain the hairy roots, and b) transforming said plant with a vector containing an expression cassette comprising a gene encoding said protein of interest, the aforesaid steps taking place in a first culture medium, and c) inducing lateral root emergences on the hairy roots in the presence of at least one auxin in liquid medium constituting a second liquid culture medium, and d) culture of the hairy roots having lateral root emergences that do not grow longer, and e) the spontaneous secretion in the medium, of the protein of interest during the culture, and f) the recovery of the aforesaid protein of interest directly from the second liquid culture medium and g) optionally, the recovery of the aforesaid protein of interest that has accumulated in the tissues, by grinding the hairy roots.

The inventors have surprisingly discovered that the culture of hairy roots of plants of the family of the Brassicaceae, obtained following infection with *R. rhizogenes*, in a liquid medium containing at least one auxin, induced the disappearance of the root hairs and the development of particular structures that are conical in shape, which are referred to hereafter by the expression "lateral root emergences" (LREs). These conical structures develop along the hairy roots and have morphological characteristics that make them in particular integral with the roots on which they develop, which clearly differentiates them from the friable calluses which are spherical, homogeneous, without differentiated cells.

Even more surprisingly, they have discovered that said lateral root emergences were capable of producing proteins of interest in larger quantities than conventional hairy roots, i.e. usually obtained during an infection with *R. rhizogenes*. In fact, they have found that significant fluorescence, linked to the production of the protein of interest, was present in the agar medium, which would suggest that the protein easily diffused from the roots modified in this way.

The morphological characteristics of the lateral root emergences and use thereof for producing a protein of interest constitute the originality of this invention.

Transformation with *Rhizobium rhizogenes* is a technique known in the state of the art. A person skilled in the art is familiar with the different techniques commonly used for carrying out said transformation step. According to the species to be transformed, the different parts of the plant can be used for the infection (hypocotyls, leaves etc.).

Generally, infection with *R. rhizogenes* is carried out by applying an inoculum of *R. rhizogenes* to plant tissues that have been wounded beforehand.

By *Rhizobium rhizogenes* is also meant *Agrobacterium rhizogenes*, former name of this bacterial species before taxonomic changes to the genus *Agrobacterium* and the family of the Rhizobiaceae.

As used here, the expression "plant belonging to the family of the Brassicaceae" has the general meaning used in the state of the art. It covers any plant of the family of the Brassicaceae formerly known as cruciferous.

It contains more than 330 genera and approximately 3700 species, according to Kew Royal Botanic Gardens. The plants belonging to the family of the Brassicaceae are for example cabbage, turnip, rape, mustard, horseradish, cress, radish, rocket, rutabaga.

The largest genera are *Draba* (365 species), *Cardamine* (200 species, but its definition is controversial), *Erysimum* (225 species), *Lepidium* (230 species) and *Alyssum* (195 species).

Well-known genera are for example *Arabidopsis, Armoracia* (horseradish genus), *Barbarea* (land cress genus), *Brassica* (cabbage, mustard, turnip, kohlrabi, rape, rutabaga), *Crambe* (crambe maritima or sea kale), *Eruca* (rocket), *Erysinum* (wallflower), *Raphanus* (radish), *Nasturtium, Wasabia* (wasabi).

Well-known species are for example *Brassica oleracea* (cabbage, cauliflower, etc.), *Brassica rapa* (turnip, Chinese cabbage, etc.), *Brassica napus* (rape, etc.), *Raphanus sativus* (common radish), *Armoracia rusticana* (horseradish), *Matthiola logipetala* (night-scented stock), *Arabidopsis thaliana* (model organism in genetics).

As used here, the expression "protein of interest" corresponds to any protein that can be produced by the method according to the invention. The protein of interest can thus equally well be a protein endogenous to the plant, or a heterologous protein.

In the case where the protein of interest is a protein endogenous to the plant, i.e. produced naturally by the plant, the plant of the family of the Brassicaceae modified by the method according to the invention, with respect to an unmodified plant, will overproduce and will secrete said endogenous protein.

In the case where the protein of interest is a heterologous protein, also called recombinant protein, the plant modified by the method according to the invention will produce a protein usually not present in the plant belonging to the family of the Brassicaceae.

This protein of interest can be any protein of plant or animal origin, including the proteins that are complex in terms of three-dimensional structure, including the proteins having disulphide bridges or associations of chains or glycosylation sites, in particular monoclonal antibodies or enzymes having a function of the hydrolase, oxydoreductase, transferase or esterase type, or transport functions such as for example sulphatases involved in rare diseases or digestive enzymes.

The term "auxin" used here denotes a plant hormone, or phytohormone, which plays a major role in controlling the growth and development of plants. This phytohormone is involved from the first stages of embryogenesis, then controls both the organization of the apical meristem (phyllotaxy) and branching of the aerial parts of the plant (apical dominance), and the formation of the main root, the initiation of the lateral roots and adventitious roots (rhizogenesis). Auxin is also involved in the tropisms in response to gravity (gravitropism) or to light (phototropism). These multiple effects at the scale of the plant result from the control that it exercises over cell, division, cell elongation and certain stages of differentiation. Different types of auxin exist.

The expression "rol genes" used here has the general meaning known from the prior art. It refers to the group of bacterial genes that are capable of inducing the formation of hairy roots (Schmulling et al., 1988; Boulgakov et al., 2008).

Typically, the rol genes are borne by a plasmid such as a pRi plasmid endogenous to the strains of *R. rhizogenes*.

As used here, the term "expression cassette" has the general meaning used in the state of the art. It refers to a nucleic acid construction which, when present in a given cell, under appropriate conditions, allows the expression of a gene of interest. According to the present invention, said gene of interest is the gene encoding a protein of interest which it is desired to produce and collect.

The expression cassette comprises a promotor, optionally a sequence encoding a signal peptide, a polylinker, and a polyadenylation signal, all in a vector plasmid.

The expression "spontaneous secretion" in the medium of the protein of interest means that said protein of interest produced by the plant cells is secreted naturally by the plant organism in its culture medium by its secretion system by default, i.e. by way of the endoplasmic reticulum and the Golgi apparatus.

The proteins of interest produced in the roots can be recovered by grinding the tissues, followed by centrifugation to remove the insoluble fraction. The protein can then be purified from the soluble fraction by chromatography techniques.

In an embodiment, the culture medium containing said protein of interest is recovered and is used directly for future applications.

In an embodiment variant, the protein of interest is obtained after one or more purification steps. Typically, the culture medium can first be clarified by standard filtration or low-speed centrifugation to remove the cell debris. The protein of interest is then either precipitated using a high saline concentration, then dialyzed, i.e. directly fixed on an affinity chromatography column. The concentrated protein of interest can then be lyophilized or stored in an appropriate storage buffer at a low temperature.

Protocols adapted to each protein of interest that can be obtained according to the invention, and for each type of application envisaged, are standard techniques of the state of the art, and a person skilled in the art will easily select the appropriate purification step(s) for the desired application.

An advantage of the present invention is simplifying the recovery and the downstream treatment of the protein of interest. Another advantage is that the root biomass is not destroyed by the recovery of the proteins and a given culture can be used for several cycles of production of said protein of interest. Unlike plants cultivated in places where the environmental factors (changes in temperature, drought, attacks by pests, pesticides/use of herbicides etc.) can considerably influence the level of production of the protein of interest, the conditions for culture of the transgenic roots in bioreactors are controlled and standardized, thus allowing a homogeneous production between the different batches. Furthermore, the roots do not produce pollen and cannot survive outside the bioreactor, which removes the risk of dissemination of the transgene into the environment.

Another advantage of the method according to the invention lies in the fact that the lines originating from hairy roots have a greater genetic stability than conventional cell lines or callus lines. The development of lateral root emergences will only be induced by the addition of hormones for the production of the protein of interest, unlike the cell lines or callus lines that must be continuously maintained on a medium rich in hormones, which induces genetic instability.

Another advantage of the method according to the invention is the possibility of producing biopharmaceutical products for delivery by oral route using species of plants that provide edible roots generally found in human/animal diets. In this case, it is not necessary to purify the protein of interest.

The use of species of edible plants in human/animal food for hundreds of years, is a good indication of their inoffensive nature, unlike tobacco which was widely used for this type of application in the past, and which belongs to the family of the Solanaceae, certain species of which are well known for their ability to produce potentially toxic compounds (alkaloids), such as nicotine.

The use of an edible plant root system for the production of proteins of therapeutic interest thus reduces the problems of health and food safety with respect to the starting raw material used, before the purification of the proteins (no animal viruses).

Thus, advantageously, the method according to the invention makes it possible to obtain high levels of proteins of interest, with reduced purification and lower costs of downstream treatment. It also makes it possible to obtain a new formulation of biopharmaceutical products for delivery by oral route, reducing the problems of human health and environmental safety.

According to a particular embodiment, a subject of the present invention is a method for producing protein of interest from lateral root emergences appearing on hairy roots of a plant belonging to the family of the Brassicaceae, in liquid medium containing at least one auxin, comprising the steps of:
  a) transforming a plant belonging to the family of the Brassicaceae with a strain of *Rhizobium* comprising the rol genes, in order to obtain the hairy roots, and
  b) transforming said plant with a vector containing an expression cassette comprising a gene encoding said protein of interest, and
  c) culture in liquid medium of the hairy roots obtained according to steps a) and b), the aforesaid steps taking place in a first culture medium, and
  d) inducing lateral root emergences on the hairy roots in the presence of at least one auxin in liquid medium constituting a second liquid culture medium, and
  e) culture in the second liquid culture medium, of the hairy roots having lateral root emergences that do not grow longer, and
  f) the spontaneous secretion in the second liquid culture medium, of the protein of interest during the culture, and
  g) the recovery of the protein of interest directly from the second liquid culture medium, and
  h) optionally, the recovery of the aforesaid protein of interest that has accumulated in the tissues by grinding the hairy roots.

According to a particular embodiment, a subject of the present invention is a method for producing protein of interest as described above in which the strain of *Rhizobium* is a strain of the species *Rhizobium rhizogenes*.

According to a particular embodiment, a subject of the present invention is a method for producing protein of interest as above, in which the strain of *Rhizobium rhizogenes* is selected from the strains ATCC 25818, LBA 9402, A4T, A4, LBA1334, ATCC 11325, ATCC 15834 and LMG 155 and preferentially selected from the strain ATCC 25818 or the strain ICPB TR7.

According to a particular embodiment, a subject of the present invention is a method for producing protein of interest as described previously in which steps a and b are simultaneous.

According to a particular embodiment, a subject of the present invention is a method for producing protein of interest as described previously in which steps a and b are simultaneous, by transforming a plant belonging to the family of the Brassicaceae with a strain of *Rhizobium* comprising the rol genes and an expression cassette comprising a gene encoding said protein of interest, in order to obtain the hairy roots.

According to a particular embodiment, a subject of the present invention is a method for producing protein of interest in a liquid culture medium containing at least one auxin, from lateral root emergences that do not grow longer appearing on hairy roots of a plant belonging to the family of the Brassicaceae, comprising the steps of:
 a) transforming a plant belonging to the family of the Brassicaceae with a strain of *Rhizobium* comprising the rol genes and an expression cassette comprising a gene encoding said protein of interest in order to obtain the hairy roots, and
 b) culture in liquid medium of the hairy roots obtained according to step a), the aforesaid steps taking place in a first culture medium, and
 c) inducing lateral root emergences on the hairy roots in the presence of at least one auxin in liquid medium constituting a second culture medium, and
 d) culture in the second liquid culture medium, of the lateral root emergences that do not grow longer appearing on the aforesaid hairy roots, and
 e) the spontaneous secretion in the second liquid culture medium, of the protein of interest during the culture, and
 f) optionally, the recovery of the aforesaid expressed protein of interest by extraction from the tissues and directly from the second liquid culture medium.

According to a particular embodiment, a subject of the present invention is a method for producing protein of interest as described above, in which said step a is carried out before step b.

According to a particular embodiment, a subject of the present invention is a method for producing protein of interest as described previously, in which said step b is carried out before step a.

According to a particular embodiment, a subject of the present invention is a method for producing protein of interest as described previously, in which the step of inducing lateral root emergences on the hairy roots in the presence of at least one auxin in liquid medium is carried out by the addition of at least one auxin to the first liquid culture medium of the hairy roots, in order to produce the second liquid culture medium.

According to a particular embodiment, a subject of the present invention is a method for producing protein of interest as described previously, in which the step of inducing lateral root emergences on the hairy roots in the presence of at least one auxin in liquid medium is carried out by replacing a first liquid culture medium of the hairy roots with a second liquid culture medium containing at least one auxin.

According to a particular embodiment, a subject of the present invention is a method for producing protein of interest as described previously, in which the step of recovery of the aforesaid expressed protein of interest is carried out directly from the second culture medium after a spontaneous secretion during the culture and optionally by grinding the cultured tissues.

According to a particular embodiment, a subject of the present invention is a method for producing protein of interest as described previously, in which the auxin is selected from: 2,4-dichlorophenoxyacetic acid (2,4-D), 3-indoleacetic acid (IAA), indole-3-butyric acid (IBA), 1-naphthaleneacetic acid (NAA), 2,4,5-trichlorophenoxyacetic acid (2,4,5-T), 2,3,5-triiodoacetic acid, 4-chlorophenoxyacetic acid, 2-naphthoxyacetic acid, 1-naphthylacetic acid, 4-amino-3,5,6-trichloropicolinic acid, 3,6-dichloro-2-methoxybenzoic acid (Dicamba) and derivatives thereof by radical modification.

According to a particular embodiment, a subject of the present invention is a method for producing protein of interest as described previously, in which 2,4-D auxin is used at a concentration from 0.01 to 10 mg/l, in particular from 0.2 to 1 mg/l.

According to a particular embodiment, a subject of the present invention is a method for producing protein of interest as described previously, in which 2,4-D auxin is used at a concentration of 0.5 mg/l.

According to a particular embodiment, a subject of the present invention is a method for producing protein of interest as described previously, in which 2,4-D auxin is used at a concentration of 1 mg/l.

According to a particular embodiment, a subject of the present invention is a method for producing protein of interest as described previously, in which the plant belonging to the family of the Brassicaceae is selected from the genera *Arabidopsis, Armoracia, Barbarea, Brassica, Crambe, Eruca, Raphanus, Wasabia* and *Camelina*.

According to a particular embodiment, a subject of the present invention is a method for producing protein of interest as described previously, in which the plant belonging to the family of the Brassicaceae is *Brassica rapa* or *Arabidopsis thaliana*.

According to a particular embodiment, a subject of the present invention is a method for producing protein of interest as described previously, in which the expression cassette comprises a signal peptide, said signal peptide being preferentially placed upstream of the gene encoding the protein of interest.

According to a particular embodiment, a subject of the present invention is a method for producing protein of interest as described previously, in which said signal peptide is derived from a plant belonging to the family of the Brassicaceae and in particular is a signal peptide originating from pectin methyl esterase (PME) encoded by the gene At1g69940 of *Arabidopsis thaliana* or a variant thereof.

According to a particular embodiment, a subject of the present invention is a method for producing protein of interest as described previously, in which the expression cassette comprises a promoter, a signal peptide, a gene encoding said protein of interest and a polyadenylation sequence.

According to a particular embodiment, a subject of the present invention is a method for producing protein of interest as described previously, in which said promoter is a promoter derived from a virus infecting the plants belonging to the family of the Brassicaceae and in particular the promoter 35S of the cauliflower mosaic virus (CaMV).

According to a particular embodiment, a subject of the present invention is a method for producing protein of interest as described previously, in which said promoter can be replaced with another promoter that can be induced by heat or a nutrient.

According to a particular embodiment, a subject of the present invention is a method for producing protein of interest as described previously, in which the protein produced is a protein not produced naturally by the genome of the plant. It is then called a protein of interest.

According to a particular embodiment, a subject of the present invention is a method for producing protein of interest as described previously, in which the protein of interest is a protein not produced naturally by the genome of the plant before the genetic transformation of said plant.

According to a particular embodiment, a subject of the present invention is a method for producing protein of interest as described previously for a protein of interest, in which the protein of interest is a protein produced naturally by the genome of the plant before the genetic transformation of said plant, but at a low level.

According to a particular embodiment, a subject of the present invention is a method for producing protein of interest as described previously, in which the post-translation modification of the protein of interest is a glycosylation or a phosphorylation.

According to a particular embodiment, a subject of the present invention is a method for producing protein of interest as described previously, in which the sequence of the protein has been modified by at least one mutation of the gene encoding it.

According to a particular embodiment, a subject of the present invention is a method for producing protein of interest as described previously, in which the protein of interest is a protein of viral origin, in particular a protein of the hepatitis B virus referenced by Swiss-Prot accession number P03141.3.

According to a particular embodiment, a subject of the present invention is a method for producing protein of interest as described previously, in which the protein of interest is a protein of animal origin, in particular a protein originating from a mammal, said mammal being selected from the rodents, felines, canines and primates.

According to a particular embodiment, a subject of the present invention is a method for producing protein of interest as described previously, in which the protein of interest is a protein of human origin.

According to a particular embodiment, a subject of the present invention is a method for producing protein of interest as described previously, in which the protein of interest is a protein of plant origin, in particular the glycosylated plant proteins.

According to a particular embodiment, a subject of the present invention is a method for producing protein of interest as described previously, in which the plant protein of interest is lectin or papain.

According to a particular embodiment, a subject of the present invention is a method for producing protein of interest as described previously, in which the protein of interest is selected from the allergens, vaccines, enzymes, enzyme inhibitors, antibodies, antibody fragments, antigens, toxins, anti-microbial peptides, hormones, growth factors, blood proteins, receptors, signalling proteins, protein components of biomedical standards, protein components of cell culture medium, fusion or labelled proteins, cysteine-rich peptides or proteins.

According to a particular embodiment, a subject of the present invention is a method for producing protein of interest as described previously, in which the blood protein produced is albumin, the coagulation factors, immunoglobulins or transferrin.

According to a particular embodiment, a subject of the present invention is a method for producing protein of interest as described previously, in which the protein is an enzyme having a function of the hydrolase, oxydoreductase, transferase or esterase type, or enzymes having a transport function such as sulphatase, or a digestive enzyme.

According to a particular embodiment, a subject of the present invention is a method for producing protein of interest as described previously, in which the protein of interest is a monoclonal antibody.

According to a particular embodiment, a subject of the present invention is a method for producing protein of interest as described previously, in which the protein of interest has glycosylation sites.

The expression "glycosylation site" relates to an amino acid of a protein that can have a covalent bond with a carbohydrate. The most common glycosylations are N-glycosylation and O-glycosylation. N-glycosylation corresponds to the addition of an oligosaccharide having in its base a branched "N-acetyl-glucosamine" on an asparagine (Asn) contained in the sequence Asn-Xaa-Ser/Thr of a protein, Xaa being any amino acid except for Pro, Ser or Thr. O-glycosylation corresponds to the addition of carbohydrates at the level of the —OH residues of certain amino acids, serine and threonine, of the proteins.

According to a particular embodiment, a subject of the present invention is a method for producing protein of interest as described previously, in which the protein of interest has associations of chains.

An association of chains requires either the synthesis of two polypeptides in the roots followed by their association, or the maturation of a chain by cleavage in the plant, followed by the association of the two chains produced.

According to a particular embodiment, a subject of the present invention is a method for producing protein of interest as described previously, in which the proteins or peptides produced are cysteine-rich, and contain at least one disulphide bridge.

According to a particular embodiment, a subject of the present invention is a method for producing protein of interest as described previously, in which the protein of interest is lipase, pepsin or trypsin.

According to a particular embodiment, a subject of the present invention is a method for producing protein of interest as described previously, in which the protein of interest is human gastric lipase.

According to a particular embodiment, a subject of the present invention is a method for producing protein of interest as described previously, in which the protein of interest is an interleukin.

According to a particular embodiment, a subject of the present invention is a method for producing protein of interest as described previously, in which the protein of interest is an interferon.

According to a particular embodiment, a subject of the present invention is a method for producing protein of interest as described previously, in which the protein of interest is GFP (Green Fluorescent Protein).

According to a particular embodiment, a subject of the present invention is also a protein of interest as obtained by the method described previously, said protein of interest being selected from the allergens, vaccines, enzymes, enzyme inhibitors, antibodies, antibody fragments, antigens, toxins, anti-microbial peptides, hormones, growth factors, blood proteins, receptors, signalling proteins, protein components of biomedical standards, protein components of cell culture media, fusion or labelled proteins, cysteine-rich peptides or proteins particularly selected from albumin, coagulation factors, immunoglobulins, transferrin, sulphatases, digestive enzymes, monoclonal antibodies, lipases, in particular human gastric lipase, pepsin, trypsin, interleukins or interferons.

A subject of the present invention is a method of production from lateral root emergences appearing on hairy roots, in liquid medium containing at least one auxin, comprising the steps of:
a) transforming a plant belonging to the family of the Brassicaceae with a strain of *Rhizobium* comprising the rol genes, in order to obtain the hairy roots, and
b) inducing lateral root emergences that do not grow longer on the hairy roots in the presence of at least one auxin in liquid medium.

FIGURES

FIG. 1: Organization of the transfer DNA (T-DNA) of the plasmid pRP49. LB: Left Border; RB: Right Border.

FIG. 2: Morphology of roots bearing lateral root emergences, three weeks after hormonal induction by 2,4-D
A. Roots in culture. B. Roots bearing lateral root emergences.

FIG. 3: Views in longitudinal section using optical microscopy. Toluidine blue staining
A. Lateral root emergences developing at the level of the pericycle of a hairy root, two weeks after induction by 2,4-D. The arrow indicates the cortical zone of the root in deliquescence.
B. Lateral root emergences showing lines of cells (arrow) and a layer of epidermal cells (ep).

Figure 4:
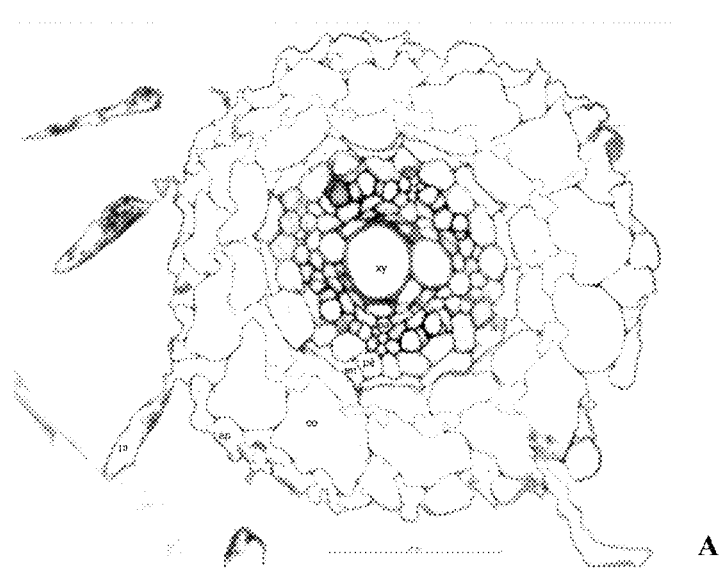
Figure 4:
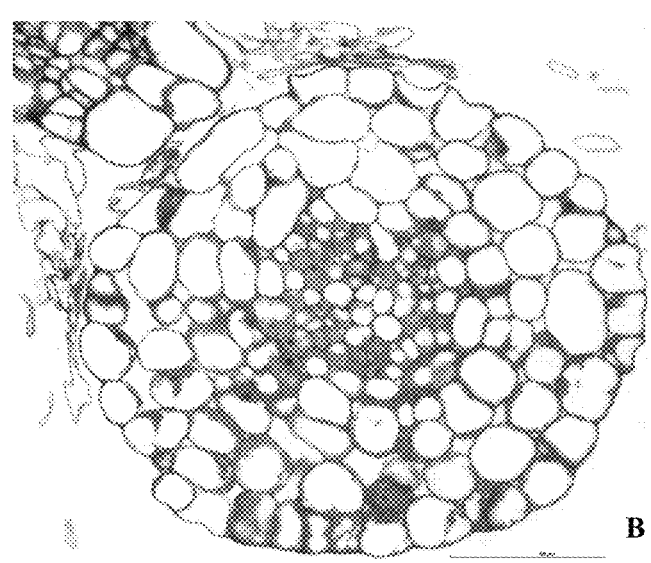

FIG. 4: Cross-sectional views using optical microscopy. Toluidine blue staining
A. Hairy root. co, cortex; en, endodermis; ep, epidermis; pa, parenchyma; pe, pericycle; pr, root hair; xy, xylem.
B. Lateral root emergence.

FIG. 5: Hairy roots producing GFP observed with an optical microscope.
A. In visible light. B. In UV light FIG. 6: Lateral root emergences containing GFB observed using optical microscopy under UV light.

Figure 7:
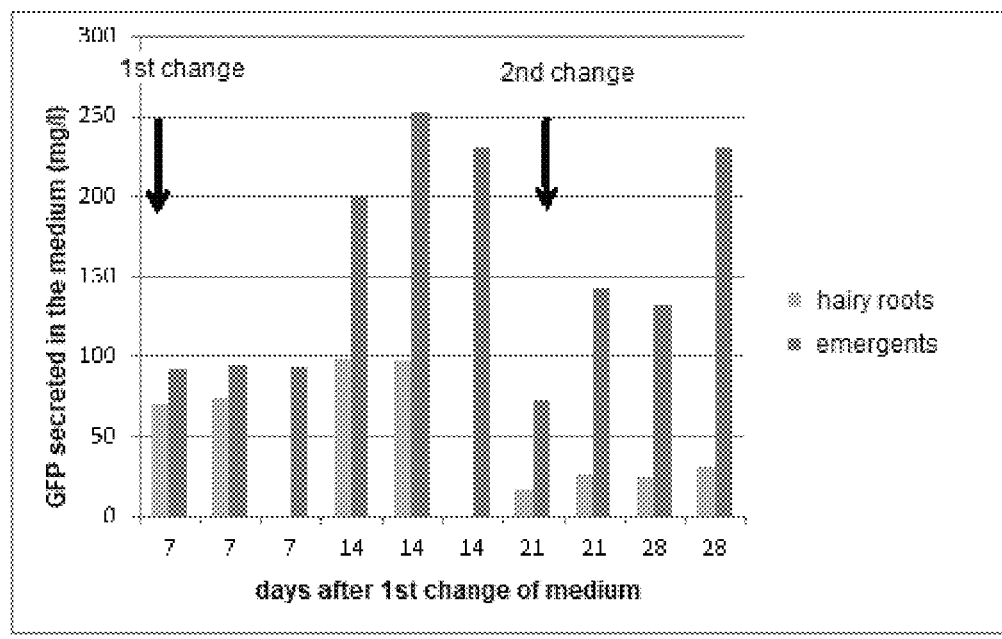

FIG. 7: GFP concentration (in mg/l) in the culture medium of hairy roots (controls), cultured in a medium without 2,4-D, and in the culture medium of hairy roots having lateral root emergences, cultured in a medium with 2,4-D, measured 1 and 2 weeks after a first renewal with a fresh identical medium, then again at 1 and 2 weeks after a second renewal with a fresh identical medium.

Figure 8:
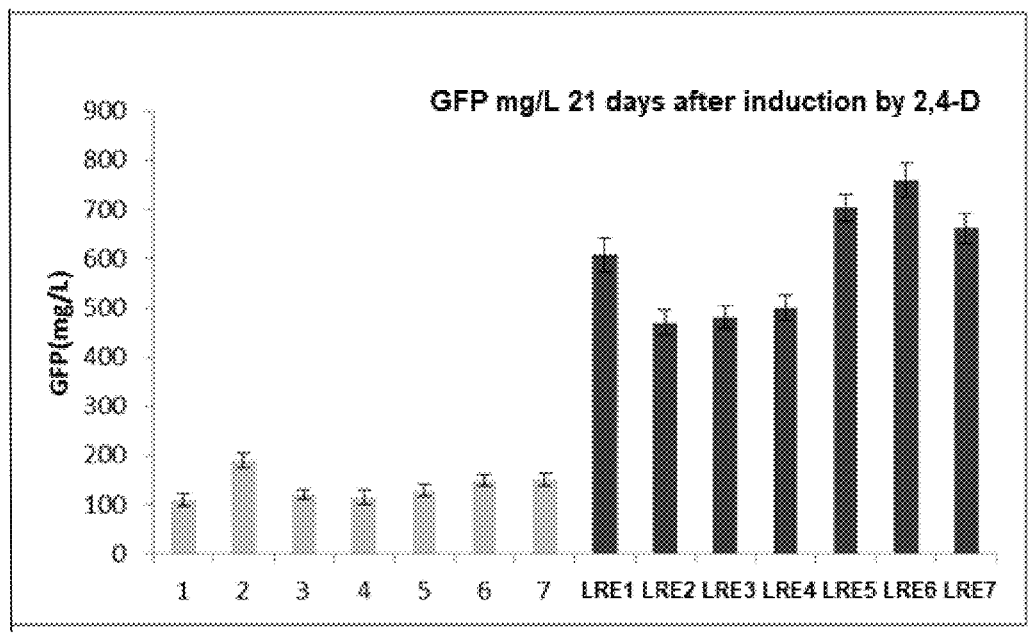

FIG. 8: GFP concentration (in mg/l) in the culture medium of hairy roots after culture for 21 days in a medium without 2,4-D (grey bars 1 to 7) (7 repetitions), and in a culture medium containing 2,4-D at 1 mg/l (black bars, LRE1 to LRE7) (7 repetitions) for inducing the development of lateral root emergences.

Figure 9:
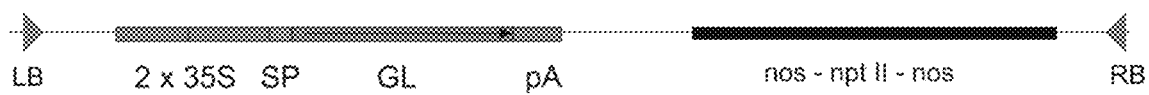

FIG. 9: Organization of the transfer DNA (T-DNA) of the plasmid pRP16. LB: Left Border; RB: Right Border.

Figure 10:
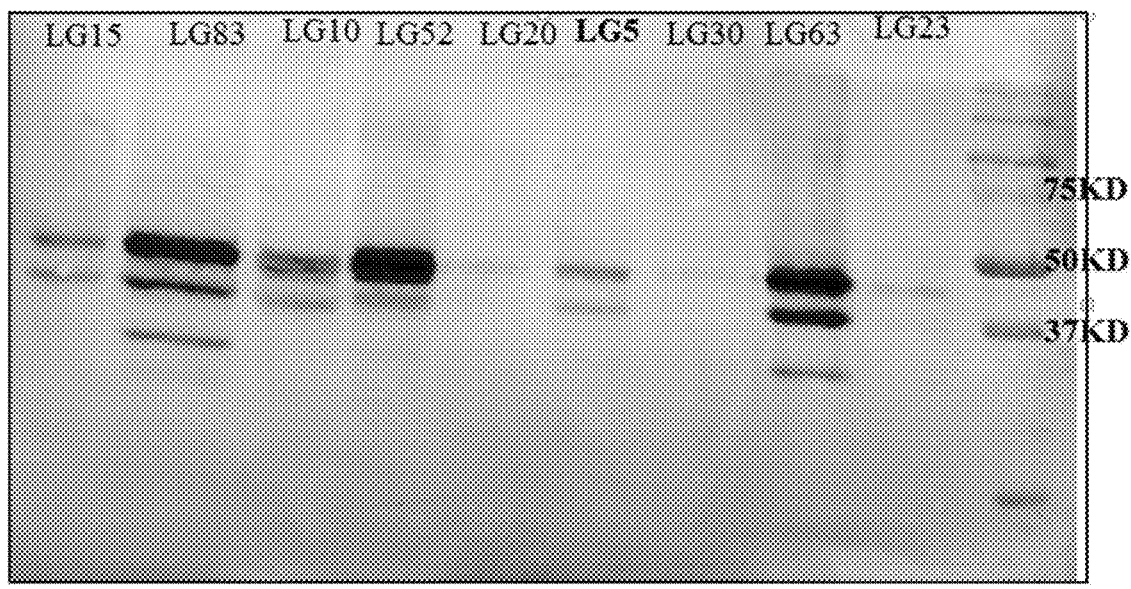

FIG. 10: Western blot of the clones secreting human gastric lipase

Figure 11:
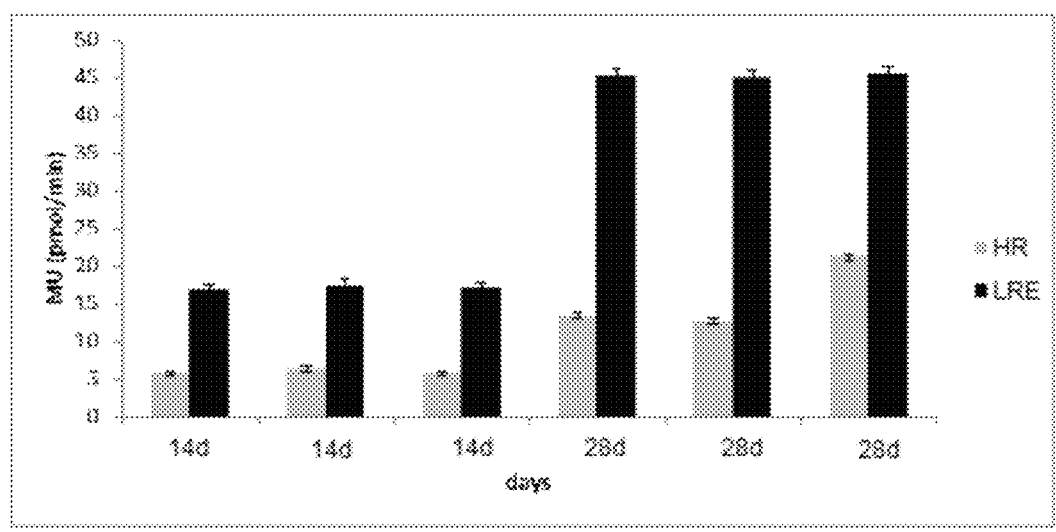

FIG. 11: Activity of human gastric lipase (pmol/min) after 14 and 28 days in the culture medium of hairy roots cultured in a medium without 2,4-D (grey bars RC) (3 repetitions), and the culture medium of hairy roots cultured in a medium with 2,4-D (1 mg/l) for inducing the development of lateral root emergences (black bars, LRE) (3 repetitions).

EXAMPLE 1

Expression of the gfp Gene

I. Material and methods
A. Recombinant Binary Plasmid for the Expression of 6× His-eGFP
The sequence encoding GFP (Green Fluorescent Protein) was cloned from the plasmid pEGFP (Clontech) and inserted into the restriction sites NcoI and EcoRI of the expression cassette pPE45 (Huet et al., 2014), in phase with the sequence encoding the signal peptide of the gene At1g69940 of *Arabidopsis thaliana* and the 6 His codons. The resultant plasmid, pRP47, was digested by Asp718 and Bg/II and the assembly 35S-SP-His-egfp-polyAa was inserted into the sites Asp718-BamHI of the binary vector pRD400 (Datla et al., 1992), producing pRP49 (SEQ ID NO: 1). In this plasmid, the expression of the egfp gene is carried out under the control of the 35S promoter of the cauliflower mosaic virus (CaMV) duplicated in its activating sequence and the expression of the nptII gene, conferring resistance to kanamycin, is carried out under the control of the nos (nopaline synthase) promoter.

The resultant plasmid, pRP49 or pRD400-gfp, has the following abovementioned sequence, SEQ ID NO: 1.

The strain of *Rhizobium rhizogenes* TR7 was transformed by electroporation with the plasmid pRP49 (FIG. 1).
B. Production, Selection and Culture of the Clone 2M1
1. Plant Species and Culture In Vitro
Table 1 below indicates the different plant families and species that were tested for the production of hairy roots (results not shown).

TABLE 1

Plant families and species tested for the production of hairy roots.

| 5 plant families | 17 plant species (abbreviations) |
| --- | --- |
| Apiaceae | *Daucus carota* (TOU) |
| Asteraceae | *Lactuca sativa* (BRU) |
| Brassicaceae | *Raphanus sativus* (CER), *Raphanus sativus* var. *niger* (NOI), *Brassica Oleracea* L. Convar (QUI), *Brassica rapa* (VER) |
| Chenopodiaceae | *Spinacia oleracea* (MAT) |
| Solanaceae | *Nicotiana tabacum* (Nt) |

As the species *Brassica rapa* (turnip) was the species for which the best hairy root production results were obtained, only *Brassica rapa* was subsequently used for the production of hairy roots.

The seeds were bought from Gondian.

Their surfaces were sterilized with 70% ethanol for 5 min, then with 7% bleach for 10 min, and washed 5 times with sterile water. The seeds were placed on solid Murashige and Skoog medium, diluted to one half (MS/2) at pH 5.8, supplemented with 1% sucrose.

The germination and growth of the seedlings was carried out at 22° C. with a photoperiod of 16 h of light/8 h of darkness.

2. Infection of the Plants with *R. rhizogenes*
The strain TR7 (ATCC 25818) of *R. rhizogenes* originating from the BCCM™/LMG collection, Laboratorium voor Microbiologie, University of Ghent, was used.

*R. rhizogenes* was cultured in a liquid MGY (Mannitol, Glutamate, Yeast) medium at pH 7.0 comprising: 2.5 g/l of yeast extract, 5 g/l of tryptone, 5 g/l of mannitol, 5 g/l of NaCl, 1.16 g/l of Na-glutamate, 0.25 g/l of $KH_2PO_4$, 0.1 g/l of MgSO$_4$, 1.0 mg/l of biotin, 8 g/l of Agar, and optionally with 50 mg/l of kanamycin added for the selection of the binary plasmid.

Inocula were prepared from 20 ml of liquid bacterial culture, cultured overnight at 25° C. in MGY medium.

The suspension was centrifuged for 5 min at 15,000 g and the cells collected were resuspended in fresh liquid MGY medium so as to obtain an optical density of 1±0.1 at 600 nm.

The infection of the *Brassica rapa* plants was carried out by pricking 3- to 10-day-old hypocotyls obtained following the culture of the seeds in step B.1, using a needle dipped in the bacterial suspension and wiping away the surplus with a cotton bud. The development of hairy roots at the level of the wounded zone was observed 7 to 10 days after the infection.

3. Selection and Culture of Clones of Hairy Roots Expressing 6× His-eGFP

The hairy roots developing on the infected hypocotyls were cut into pieces and placed individually on a Murashige and Skoog medium at pH 5.8 containing 3% sucrose and 300 mg/L of cefotaxime (MS3cef). After 7 to 10 days, 40 independent hairy root tips (clones) were transferred onto an MS3cef liquid medium where they were cultured at 23° C. in darkness for 2 to 4 weeks.

For each clone, a fragment was directly monitored using a Nikon Eclipse 90i microscope in order to observe the emission of fluorescence due to the presence of GFP.

The images were taken using a Nikon Digital Sight DS-5Mc camera.

The 10 clones exhibiting the most fluorescence were selected to be cultured in liquid medium.

In order to initiate the cultures in liquid medium, a fragment of approximately 1 cm of each hairy root clone was transferred into a Petri dish containing 5 ml of liquid Gamborg B5 medium (Duchefa) at pH 5.8 with 3% sucrose and 300 mg/l of cefotaxime (B53cef) added.

The fragments were then cultured in darkness at 23° C. for 10 days, accompanied by stirring at 56 rpm.

The hairy roots were then successively cultured in a 100 ml Erlenmeyer flask containing 20 ml of B53cef for 3 weeks, then again in a 250 ml Erlenmeyer flask containing 100 ml of B53cef at 26° C. under low light for 3 weeks, accompanied by stirring at 110 rpm.

After these steps aimed at eliminating the *Rhizobia* by the use of the antibiotic cefotaxime, the standard culture conditions were as follows: 100 ml of Gamborg B5 liquid medium with 3% sucrose added, pH 5.8 at 26° C. under low light, using a Gerhardt R020 stirrer at 110 rpm. The different clones of roots were subcultured ever 3 weeks using 1 g of biomass of roots per 100 ml of Gamborg B5 liquid culture medium with 3% sucrose added.

The clone of *Brassica rapa* having the best fluorescence emission performance was selected and named clone 2M1.

C. Induction of Lateral Root Emergences on Hairy Roots of the Clone 2M1

1. Induction of Lateral Root Emergences (LRE)

In order to modify the morphology of the hairy roots and prevent the development of the root hairs, roots of the clone 2M1 producing GFP were cultured in B53 liquid medium for two weeks. This culture medium was then removed and replaced with fresh B53 medium containing 2,4-dichlorophenoxyacetic acid (2,4-D), an auxin-type hormone, at 0.5 mg/l.

Numerous conical structures called "lateral root emergences" (LRE) then developed on the hairy roots (FIG. 2A) during the following 7 days. The "lateral root emergences" are then in the form of blisters on each root (FIG. 2B). These emergences subsequently persist without other modifications, i.e. the presence of 2,4-D auxin in the medium after the appearance of these lateral emergences, prevents the differentiation of these emergences into roots.

2. Observation Using Optical Microscopy (Comparison Between Visible and UV Light)

In order to characterize these conical structures or "lateral root emergences" developing on the roots after hormonal induction, longitudinal sections (FIG. 3) and cross sections (FIG. 4) were produced in the control hairy roots after culture for 2 weeks in B53 medium and in hairy roots having lateral root emergences after culture for 2 weeks in B53 medium with 2,4-D auxin added.

The tissues were fixed in 4% p-formaldehyde overnight at 4° C., dehydrated in baths of ethanol of increasing concentrations, then enclosed in LR White resin. Sections with a thickness of 0.5 to 1 µm were produced using a Leica RM2265 microtome, stained with toluidine blue and observed using a Nikon Eclipse 90i microscope. The images were obtained using a Nikon Digital Sight DS-5Mc device, in visible light or in fluorescence to locate the GFP.

3. Quantification by Fluorometry of the 6× His-eGFP Released in the Culture Medium by Hairy Roots Having Lateral Root Emergences For the quantification of 6× His-EGFP, culture medium was diluted to 20× or 40× in a 50 mM tris buffer at pH 7.5. The fluorescence of the solution was measured using the BioRad VersaFluor™ fluorometer (excitation filter 485-495 nm; emission filter 505-515 nm). The calibration of the fluorometer was carried out using the commercially available recombinant 6× His-EGFP (BioVision) at a concentration of 10 mg/l.

II. Results

1. Microscopic Observations

Observation in visible light, of the sections of control hairy roots, i.e. obtained in culture medium without 2,4-D, shows the tissues typical of the roots of dicotyledons, starting from the periphery: a layer of epidermal cells, a cortical zone, a layer of endodermal cells, a pericycle and a central cylinder containing the conductor bundles in the parenchyma (FIG. 4A).

The organization of the hairy roots, obtained after culture in the presence of 2,4-D auxin, is very different. The cortical zone has completely degenerated and blisters are observed at the level of the pericycle. These bulges appear to be at the origin of the conical structures, lateral root emergences, developing on the hairy roots.

The longitudinal sections (FIGS. 3A and 3B) and cross sections (FIG. 4B) produced from these conical structures show heterogeneous tissues, some of which recall those present in the roots: layer of epidermal cells, outline of central cylinder containing denser cells (FIG. 4B). The development of these structures is not disorganized: lines of cells are observed (FIG. 3A), an indication of cell divisions oriented as in the case of root tips. These are therefore lateral root emergences from certain cells of the pericycle (FIG. 3A).

These morphological characteristics clearly differentiate these conical structures or lateral root emergences from friable calluses which are spherical, homogeneous, without differentiated cells (Ikeuchi et al (2013) "Plant Callus: Mechanisms of Induction and Repression" Plant Cell 25: 3159-3173).

Microscopic observation in visible light makes it possible to show that the transformation of plant cells by *R. rhizo-*

*genes* results in the production of highly branched roots having countless root hairs and thus called control hairy roots (FIG. 5A).

Epi-fluorescence microscope observations of the control hairy roots expressing GFP showed that the root hairs, although occupying a large volume, produced no, or little, protein (FIG. 5B). However, the same microscope observations showed, on the one hand that the cells of 4-week-old roots contained little GFP and, on the other hand, that the GFP was situated substantially at the level of the central cylinder (FIG. 5B). This observation suggests that there would be less production and less diffusion in the medium of the proteins of interest when they are produced by old roots.

Conversely, observation of the hairy roots having lateral root emergences using an epi-fluorescence microscope revealed significant fluorescence (FIG. 6).

2. Quantification of GFP Secretion a. Test 1

After culture of hairy roots of the clone 2M1 in B53 liquid medium for two weeks, this medium was replaced with fresh B53 medium containing 2,4-D auxin at 0.5 mg/l, in order to induce the development of lateral root emergences. The hairy roots of the clone 2M1 were thus cultured in Petri dishes containing 5 ml of B53 medium with 2,4-D added, at 23° C. and under stirring at 56 rpm.

The GFP secreted in the culture medium by the hairy roots having lateral root emergences, was quantified (10 repetitions) one and two weeks after the addition of 2,4-D auxin at 0.5 mg/l (Table 2).

TABLE 2

Quantification of the GFP in mg/l in the culture medium, of lateral root emergences 1 and 2 weeks after the replacement of the B53 culture medium with a fresh B53 culture medium with 2,4-D auxin added.

| Petri dish (5 mL B53) | 1 week after B53 + 2,4-D | 2 weeks after B53 + 2,4-D |
|---|---|---|
| 1 | 57 | 190 |
| 2 | 58 | 185 |
| 3 | 55 | 167 |
| 4 | 48 | 144 |
| 5 | 49 | 152 |
| 6 | 51 | 158 |
| 7 | 49 | 159 |
| 8 | 59 | 169 |
| 9 | 47 | 153 |
| 10 | 50 | 161 |
| Average clones | 52 | 164 |
| Confidence interval (p = 0.95) | 3.2 | 10.3 |

Hairy roots of the clone 2M1 were cultured (9 repetitions) under the same conditions changing the B53 medium with fresh B53 medium but without the addition of auxin after culture for the first two weeks, in order to constitute control batches of hairy roots.

The GFP secreted in the culture medium by the conventional (control) hairy roots was quantified one and two weeks after the replacement with fresh B53 medium without 2,4-D (Table 3).

TABLE 3

Quantifications of the GFP in mg/l in the culture medium of control hairy roots one and two weeks after the replacement of the B53 culture medium with a fresh B53 culture medium (9 repetitions).

| | 1 week after changing the B53 medium | 2 week after changing the B53 medium |
|---|---|---|
| 1 | 48 | 123 |
| 2 | 50 | 150 |
| 3 | 58 | 146 |
| 4 | 46 | 159 |
| 5 | 36 | 168 |
| 6 | 40 | 161 |
| 7 | 32 | 153 |
| 8 | 25 | 128 |
| 9 | 22 | 143 |
| Averages | 40 | 148 |
| Confidence interval | 9.2 | 11.5 |

The concentration of GFP in the culture medium of the hairy roots of the clone 2M1, two weeks after the addition of 2,4-D auxin was 164±10.3 mg/l (n=10).

The concentration of GFP in the culture medium of the control hairy roots of the clone 2M1, two weeks after the replacement of the B53 medium with fresh B53 medium, was 148±11.5 mg/l (n=9). This production by the roots, greater than what was published (~120 mg/l; Huet et al., 2014), is due to the renewal of the medium after culture for two weeks.

The comparison, by a Student's test, of the results obtained for the hairy roots of the clone 2M1 cultured in the presence of 2,4-D, and then having lateral root emergences, relative to those obtained for the control hairy roots, show a significant difference (p<0.05): a greater quantity of GFP is found in the culture medium of the hairy roots bearing the lateral root emergences than in the medium of the control hairy roots, i.e. without lateral root emergences.

b. Test 2

The clone 2M1 was inoculated at t0 into 5 Erlenmeyer flasks at a rate of 2 g of fresh roots in 100 ml of B53 medium. After culture at 26° C. with a stirrer at 110 rpm for 15 days, the roots have reached a mass of 24.4 g+/−3.90.

A first change of medium was then carried out in each of the flasks as follows;
in two flasks, the B53 medium was replaced with fresh B53 medium in order to carry out two repetitions for the control hairy roots;
in three flasks, the B53 medium was replaced with B53 medium with 2,4-D added at 1 mg/l in order to carry out three repetitions for inducing the development of lateral root emergences;

The GFP secreted in the culture medium was quantified 7 to 14 days after this first change of medium.

A second change of medium was then carried out in these same flasks, in an identical manner:
in the two flasks of control hairy roots. the B53 medium was replaced with fresh B53 medium;
in the three flasks of induced hairy roots, the B53 medium with 2,4-D added at 1 mg/l was replaced with B53 medium with fresh 2,4-D added at 1 mg/l;

All of the results are shown in FIG. 7.

Under these conditions, the secretion of GFP by the cultures treated with 2,4-D is doubled after treatment for 14 days. This observation is accentuated after the second renewal of culture medium, where the secretion is increased by a factor of 5 to 9.

c. Test 3

Roots of the clone 2M1 were inoculated in 14 Petri dishes, each containing 5 ml of liquid B53 culture medium. They were cultured at 26° C. under stirring at 110 rpm for 17 days.

The medium was then changed in the Petri dishes as follows:

in seven Petri dishes, the medium was removed and replaced with fresh B53 culture medium with 2,4-D added at 1 mg/l (LRE 1 to 7) in order to induce the development of lateral root emergences in these dishes;

and in the other seven Petri dishes, the medium was removed and replaced with fresh B53 culture medium (Controls 1 to 7).

The roots were maintained at 26° C. under stirring at 110 rpm for 21 days.

FIG. 8 shows the concentrations of GFP in the culture medium, after culture for these 21 days.

After 21 days, the concentration of GFP in the medium of the roots having lateral root emergences induced by the presence of 2,4-D in the culture medium, is 4.3 times greater (597 mg/l+/−116) than that in the culture medium of control hairy roots, i.e. without lateral root emergences (138 mg/l+/−28).

EXAMPLE 2

Expression of the Human Gastric Lipase Gene

I. Material and Methods

A. Recombinant Binary Plasmid for the Expression of 6× His-Lipase

The sequence of the gene encoding human gastric lipase (GL) was synthesized by DNA2.0 in the form of a fusion with the sequence encoding the signal peptide of the gene At1g69940 of *Arabidopsis* (SP). The hybrid sequence was then inserted, in the expression cassette pJIT163 (Guerineau et al., 1992), into the restriction sites NcoI and EcoRI, to give the plasmid pRP9. The assembly 2×35S-SP-GL-polyA contained in a fragment of the plasmid pRP9 bordered by the restriction sites KpnI-Bg/II was then inserted at the KpnI-BamHI sites of the binary plasmid pRD400, in order to create the plasmid pRP16 (FIG. 9).

The synthesized gene GL-SP has the following sequence SEQ ID NO: 2.

The strain TR7 of *Rhizobium rhizogenes* was then transformed by electroporation (2.5 kV, for approximately 5 msec) with the plasmid pRP16.

B. Production, Selection and Culture of the Clone LG5

1. Plant Species and Culture In Vitro

The species *Brassica rapa* (turnip) was used for producing hairy roots according to the same protocol as previously (Example 1 part I.B. 1.).

The seeds were bought from Gondian.

Their surfaces were sterilized with 70% ethanol for 5 min, then with 7% bleach for 10 min, and washed 5 times with sterile water. The seeds were placed on solid Murashige and Skoog medium, diluted to one half (MS/2) at pH 5.8, supplemented with 1% sucrose.

The germination and growth of the seedlings was carried out at 22° C. with a photoperiod of 16 h of light/8 h of darkness.

2. Infection of the Plants with *R. rhizogenes*

The strain TR7 (ATCC 25818) of *R. rhizogenes* originating from the BCCM™/LMG collection, Laboratorium voor Microbiologie, University of Ghent, was used.

*R. rhizogenes* was cultured in a liquid MGY medium at pH 7.0 composed of 2.5 g/l of yeast extract, 5 g/l of tryptone, 5 g/l of mannitol, 5 g/l of NaCl, 1.16 g/l of Na-glutamate, 0.25 g/l of $KH_2PO_4$, 0.1 g/l of $MgSO_4$, 1.0 mg/l of biotin, 8 g/l of Agar, and optionally with 50 mg/l of kanamycin added for the selection of the binary plasmid.

Inocula were prepared from 1.5 ml of liquid bacterial culture, cultured overnight at 28° C. in liquid MGY medium.

The suspension was centrifuged for 1 min at 10,000 g and the cells collected were resuspended in 100 µl of liquid Gamborg B5 medium (Duchefa) at pH 5.7 containing 1% sucrose.

The infection of the *Brassica rapa* plants was carried out by pricking 10-day-old hypocotyls obtained following the culture of the seeds in step B.1. (Example 2), using a needle dipped in the bacterial suspension and wiping away the surplus with a cotton bud.

The hairy root emergence at the level of the wounded zone was observed 7 to 15 days after the infection.

3. Selection and Culture of Clones of Hairy Roots Expressing 6× His-Lipase

The hairy roots developing on the infected hypocotyls were cut into pieces and placed on a solid Gamborg B5 medium containing 3% sucrose and 300 mg/L of cefotaxime. After culture for 7 to 10 days, 15 to 40 independent hairy root tips (clones) were transferred onto a liquid Gamborg B5 medium containing 3% sucrose and 300 mg/L of cefotaxime where they were cultured for 2 to 4 weeks.

They were then cultured and subcultured regularly every 3 weeks in the same fresh medium for 3 months until the cefotaxime was eliminated.

The root hair clone was then considered stabilized and is maintained by successive subculture every 3 weeks in liquid Gamborg B5 medium containing 3% sucrose.

The presence of human gastric lipase, in the liquid culture medium of the roots used for this study, was confirmed by Western blot using an anti-human gastric lipase monoclonal antibody (FIG. 10).

The culture media of the clones are recovered then concentrated 10 times with Amicon filters (10K) A migration on gel of 10 µl of concentrated medium was carried out by electrophoresis under denaturing conditions. After the migration, a print of this gel was made by transfer onto a nitrocellulose membrane. The human gastric lipase was identified on the nitrocellulose membrane by the Western Blotting method, successively using a first anti-human gastric lipase monoclonal antibody (wh0008513M1, Sigma), then a second antibody coupled to peroxidase (A9044, Sigma) directed against the first antibody. The human gastric lipase is then developed by means of the appearance of a coloured product originating from the reaction between the peroxidase and the substrates diaminobenzidine and urea/$H_2O_2$.

The clone LG5 was selected for having the highest secretion rate.

C. Induction of Lateral Root Emergences on Hairy Roots of LG5 and Characterization Thereof 1. Induction of Lateral Root Emergences on Hairy Roots For this study, a subculture was carried out in six empty Erlenmeyer flasks, to which 1 g of biomass of the same mass of roots of the clone LG5 and 100 ml of liquid Gamborg B53 medium are added. The roots are cultured at 26° C. and under stirring at 110 rpm for two weeks.

In order to induce the development of lateral root emergences (LRE) in three Erlenmeyer flasks, this liquid medium is replaced with fresh B53 culture medium containing 2,4-dichlorophenoxyacetic acid (2,4-D) at 1 mg/l.

In the other three Erlenmeyer flasks having conventional hairy roots (HR), it is replaced with fresh B53 liquid culture medium, without 2,4-D.

After culture for two weeks at 26° C. with stirring at 110 rpm, a second change of medium was carried out in the flasks in an identical manner, in order to replace the culture medium with a fresh culture medium with +/−2,4-D at 1 mg/l.

2. Quantification of the Gastric Lipase Activity

The activity of the human gastric lipase is measured directly from the liquid culture media in the 6 flasks (14 days and 28 days after induction). The enzymatic activity is measured at 37° C. using 4-methylumbelliferyl oleate (0.1 mM) as substrate. The fluorescence of the 4-methylumbelliferone (MU), product of the enzyme reaction by the gastric lipase, is measured with a fluorometer (Excitation: 330 nm; Emission: 450 nm). This fluorescence is correlated to the human gastric lipase activity (FIG. 11).

II. Results

The activity of the human gastric lipase was measured in the liquid culture media of the hairy roots having lateral root emergences (LRE1, LRE2 and LRE3) and conventional hairy roots (HR1, HR2 and HR3). This activity is measured 14 and 28 days after induction by the addition of 2,4-D (FIG. 11).

At 14 days, in the Erlenmeyer flasks the medium of which has not been supplemented with 2,4-D, and containing conventional hairy roots (HR) (controls), the activity of the human gastric lipase is 6±0.3 pmol/min (MU).

On the other hand, in the Erlenmeyer flasks the medium of which has been supplemented with 2,4-D, and containing lateral root emergences (LRE), the activity of the human gastric lipase is 16±0.6 pmol/min.

At 28 days, in the Erlenmeyer flasks containing conventional roots (controls) the activity of the human gastric lipase is 17±0.3 pmol/min, whereas in the Erlenmeyer flasks containing lateral root emergences, the activity of the human gastric lipase is 45±0.3 pmol/min.

This study shows that the activity of the human gastric lipase measured in the liquid medium of the lateral root emergences (LRE) is approximately 3 times greater than that measured with conventional hairy roots (HR).

The invention claimed is:

1. A method for producing a protein of interest from lateral root emergences appearing on hairy roots of a plant belonging to the family of the Brassicaceae, in liquid medium containing at least one auxin, comprising the steps of:

a) transforming a plant belonging to the family of the Brassicaceae with a strain of *Rhizobium* capable of inducing hairy root growth on said plant, in order to obtain the hairy roots, and b) transforming said plant with a vector containing an expression cassette comprising a gene encoding said protein of interest or a vector containing an expression cassette comprising a sequence encoding a signal peptide and a gene encoding said protein of interest, the aforesaid steps taking place in a first culture medium, and
  c) inducing lateral root emergences on the hairy roots in the presence of at least one auxin in liquid medium constituting a second liquid culture medium, thereby to prevent the lateral root emergences from differentiating into roots, and either
  d) recovering said protein of interest that has accumulated in tissues of said lateral root emergences by grinding the hairy roots when said vector contains an expression cassette comprising a gene encoding said protein of interest, or
  e) recovering said protein of interest spontaneously secreted directly from the second liquid culture medium when said vector contains an expression cassette comprising a sequence encoding a signal peptide and a gene encoding said protein of interest.

2. The method for producing a protein of interest according to claim 1, in which the strain of *Rhizobium* is a strain of the species *Rhizobium rhizogenes*.

3. The method for producing a protein of interest according to claim 1, in a liquid culture medium containing at least one auxin, from lateral root emergences appearing on hairy roots of a plant belonging to the family of the Brassicaceae, comprising the steps of:
  a) transforming a plant belonging to the family of the Brassicaceae with a strain of *Rhizobium* capable of inducing hairy root growth on said plant and comprising an expression cassette comprising a gene encoding said protein of interest in order to obtain the hairy roots or an expression cassette comprising a sequence encoding a signal peptide and a gene encoding said protein of interest, and
  b) culturing in liquid medium the hairy roots obtained according to step a),
the aforesaid steps taking place in a first culture medium, and
  c) inducing lateral root emergences on the hairy roots in the presence of at least one auxin in liquid medium, constituting a second culture medium, thereby to prevent the lateral root emergences from differentiating into roots, and either
  d) recovering said protein of interest that has accumulated in tissues of said lateral root emergences by grinding the hairy roots when said expression cassette comprising a gene encoding said protein of interest, or
  e) recovering said protein of interest spontaneously secreted directly from the second liquid culture medium when said expression cassette comprising a sequence encoding a signal peptide and a gene encoding said protein of interest.

4. The method for producing a protein of interest according to claim 1, in which the step of inducing lateral root emergences on the hairy roots in the presence of at least one auxin in liquid medium is carried out by the addition of at least one auxin to the first liquid culture medium of the hairy roots, in order to produce the second liquid culture medium.

5. The method for producing a protein of interest according to claim 1, in which the step of inducing lateral root emergences on the hairy roots in the presence of at least one auxin in liquid medium is carried out by replacing a first liquid culture medium of the hairy roots with a second liquid culture medium containing at least one auxin.

6. The method for producing a protein of interest according to claim 1, in which the auxin is selected from: 2,4-dichlorophenoxyacetic acid (2,4-D), 3-indoleacetic acid (IAA), indole-3-butyric acid (IBA), 1-naphthaleneacetic acid (NAA), 2,4,5-trichlorophenoxyacetic acid (2,4,5-T), 2,3,5-triiodoacetic acid, 4-chlorophenoxyacetic acid, 2-naphthoxyacetic acid, 1-naphthylacetic acid, 4-amino-3,5,6-trichloropicolinic acid, 3,6-dichloro-2-methoxybenzoic acid (Dicamba).

7. The method for producing a protein of interest according to claim 1, in which the auxin is the 2,4-D auxin which is used at a concentration from 0.01 to 10 mg/l.

8. The method for producing a protein of interest according to claim 1, in which the plant belonging to the family of the Brassicaceae is selected from the genera *Arabidopsis, Armoracia, Barbarea, Brassica, Crambe, Eruca, Raphanus, Wasabia* and *Camelina*.

9. The method for producing a protein of interest according to claim 1, in which the plant belonging to the family of the Brassicaceae is *Brassica rapa* or *Arabidopsis thaliana*.

10. The method for producing a protein of interest according to claim 1, in which the protein of interest is a protein of viral origin, or a protein of animal origin, or a protein of human origin, or a protein of plant origin.

11. The method for producing a protein of interest according to claim 1, in which the protein of interest is selected from allergens, vaccines, enzymes, enzyme inhibitors, antibodies, antibody fragments, antigens, toxins, antimicrobial peptides, hormones, growth factors, blood proteins, receptors, signalling proteins, protein components of biomedical standards, protein components of cell culture medium, fusion proteins, labelled proteins, cysteine-rich peptides and cysteine-rich proteins.

12. The method for producing a protein of interest according to claim 1, in which the protein of interest is human gastric lipase.

13. The method of claim 1, further comprising a step of recovering the aforesaid protein of interest that has accumulated in the tissues of said lateral root emergences by grinding the hairy roots when said vector contains an expression cassette comprising a sequence encoding a signal peptide and a gene encoding said protein of interest.

14. The method of claim 3, further comprising a step of recovering the aforesaid expressed protein that has accumulated in the tissues of said lateral root emergences by grinding the hairy roots when said expression cassette comprising a sequence encoding a signal peptide and a gene encoding said protein of interest.

15. The method for producing a protein of interest according to claim 1, in which the strain of *Rhizobium* is a strain of the species *Rhizobium rhizogenes* selected from the strains ATCC 25818, LBA 9402, A4T, A4, LBA1334, ATCC 11325, ATCC 15834, LMG 155 and ICPB TR7.

16. The method for producing a protein of interest according to claim 1, in which the strain of *Rhizobium* is a strain of the species *Rhizobium rhizogenes* selected from the strains ATCC 25818 and ICPB TR7.

17. The method for producing a protein of interest according to claim 1, in which the auxin is the 2,4-D auxin which is used at a concentration from 0.2 to 1 mg/l.

18. The method for producing a protein of interest according to claim 1, in which the auxin is the 2,4-D auxin which is used at a concentration of 0.5 mg/l or at a concentration of 1 mg/l.

19. The method for producing a protein of interest according to claim 1, in which the protein of interest is a protein of animal origin, said animal being a mammal and said mammal being selected from the rodents, felines, canines and primates.

* * * * *

SEQUENCE LISTING

```
<160> NUMBER OF SEQ ID NOS: 2

<210> SEQ ID NO 1
<211> LENGTH: 13583
<212> TYPE: DNA
<213> ORGANISM: artificial sequence
<220> FEATURE:
<223> OTHER INFORMATION: pRD400-gfp

<400> SEQUENCE: 1
ccgggctggt tgccctcgcc gctgggctgg cggccgtcta tggccctgca aacgcgccag      60
aaacgccgtc gaagccgtgt gcgagacacc gcggccgccg gcgttgtgga tacctcgcgg     120
aaaacttggc cctcactgac agatgagggg cggacgttga cacttgaggg gccgactcac     180
ccggcgcggc gttgacagat gaggggcagg ctcgatttcg gccggcgacg tggagctggc     240
cagcctcgca aatcggcgaa aacgcctgat tttacgcgag tttcccacag atgatgtgga     300
caagcctggg gataagtgcc ctgcggtatt gacacttgag gggcgcgact actgacagat     360
gaggggcgcg atccttgaca cttgaggggc agagtgctga cagatgaggg gcgcacctat     420
tgacatttga ggggctgtcc acaggcagaa aatccagcat ttgcaagggt ttccgcccgt     480
ttttcggcca ccgctaacct gtcttttaac ctgcttttaa accaatattt ataaaccttg     540
tttttaacca gggctgcgcc ctgtgcgcgt gaccgcgcac gccgaagggg ggtgcccccc     600
cttctcgaac cctcccggcc cgctaacgcg ggcctcccat cccccagggg gctgcgcccc     660
tcggccgcga acggcctcac cccaaaaatg gcagcgctgg cagtccttgc cattgccggg     720
atcggggcag taacgggatg ggcgatcagc ccgagcgcga cgcccggaag cattgacgtg     780
ccgcaggtgc tggcatcgac attcagcgac caggtgccgg gcagtgaggg cggcggcctg     840
ggtggcggcc tgcccttcac ttcggccgtc ggggcattca cggacttcat ggcggggccg     900 gcaatttta ccttgggcat tcttggcata gtggtcgcgg gtgccgtgct cgtgttcggg     960
ggtgcgataa acccagcgaa ccatttgagg tgataggtaa gattataccg aggtatgaaa    1020
acgagaattg gacctttaca gaattactct atgaagcgcc atatttaaaa agctaccaag    1080
acgaagagga tgaagaggat gaggaggcag attgccttga atatattgac aatactgata    1140
agataatata tcttttatat agaagatatc gccgtatgta aggatttcag ggggcaaggc    1200
```

```
ataggcagcg cgcttatcaa tatatctata gaatgggcaa agcataaaaa cttgcatgga    1260
ctaatgcttg aaacccagga caataacctt atagcttgta aattctatca taattgggta    1320
atgactccaa cttattgata gtgttttatg ttcagataat gcccgatgac tttgtcatgc    1380
agctccaccg attttgagaa cgacagcgac ttccgtccca gccgtgccag gtgctgcctc    1440
agattcaggt tatgccgctc aattcgctgc gtatatcgct tgctgattac gtgcagcttt    1500
cccttcaggc gggattcata cagcggccag ccatccgtca tccatatcac cacgtcaaag    1560
ggtgacagca ggctcataag acgccccagc gtcgccatag tgcgttcacc gaatacgtgc    1620
gcaacaaccg tcttccggag actgtcatac gcgtaaaaca gccagcgctg gcgcgattta    1680
gccccgacat agccccactg ttcgtccatt ccgcgcaga cgatgacgtc actgcccggc     1740
tgtatgcgcg aggttaccga ctgcggcctg agttttttaa gtgacgtaaa atcgtgttga    1800
ggccaacgcc cataatgcgg gctgttgccc ggcatccaac gccattcatg gccatatcaa    1860
tgattttctg gtgcgtaccg ggttgagaag cggtgtaagt gaactgcagt tgccatgttt    1920
tacggcagtg agagcagaga tagcgctgat gtccggcggt gcttttgccg ttacgcacca    1980
ccccgtcagt agctgaacag gagggacagc tgatagacac agaagccact ggagcacctc    2040
aaaaacacca tcatacacta aatcagtaag ttggcagcat cacccataat tgtggtttca    2100
aaatcggctc cgtcgatact atgttatacg ccaactttga aaacaacttt gaaaaagctg    2160
ttttctggta tttaaggttt tagaatgcaa ggaacagtga attggagttc gtcttgttat    2220
aattagcttc ttggggtatc tttaaatact gtagaaaaga ggaaggaaat aataaatggc    2280
taaaatgaga atatcaccgg aattgaaaaa actgatcgaa aaataccgct gcgtaaaaga    2340
tacggaagga atgtctcctg ctaaggtata taagctggtg ggagaaaatg aaaacctata    2400
tttaaaaatg acgacagcc ggtataaagg gaccacctat gatgtggaac gggaaaagga    2460
catgatgcta tggctggaag gaaagctgcc tgttccaaag gtcctgcact ttgaacggca    2520
tgatggctgg agcaatctgc tcatgagtga ggccgatggc gtcctttgct cggaagagta    2580
tgaagatgaa caaagccctg aaaagattat cgagctgtat gcggagtgca tcaggctctt    2640
tcactccatc gacatatcgg attgtcccta tacgaatagc ttagacagcc gcttagccga    2700
attggattac ttactgaata acgatctggc cgatgtggat tgcgaaaact gggaagaaga    2760
cactccattt aaagatccgc gcgagctgta tgattttta aagacggaaa agcccgaaga    2820
ggaacttgtc ttttcccacg cgacctggg agacagcaac atctttgtga agatggcaa     2880 agtaagtggc tttattgatc ttgggagaag cggcagggcg gacaagtggt atgacattgc    2940
cttctgcgtc cggtcgatca gggaggatat cggggaagaa cagtatgtcg agctatttt     3000 tgacttactg gggatcaagc ctgattggga gaaataaaa tattatattt tactggatga     3060
attgttttag tacctagatg tggcgcaacg atgccggcga caagcaggag cgcaccgact    3120
tcttccgcat caagtgtttt ggctctcagg ccgaggccca cggcaagtat ttgggcaagg    3180
ggtcgctggt attcgtgcag ggcaagattc ggaataccaa gtacgagaag gacggccaga    3240
cggtctacgg gaccgacttc attgccgata aggtggatta tctggacacc aaggcaccag    3300
gcgggtcaaa tcaggaataa gggcacattg ccccggcgtg agtcgggca atcccgcaag     3360 gagggtgaat gaatcggacg tttgaccgga aggcatacag gcaagaactg atcgacgcgg    3420
ggttttccgc cgaggatgcc gaaaccatcg caagccgcac cgtcatgcgt gcgccccgcg    3480
aaaccttcca gtccgtcggc tcgatggtcc agcaagctac ggccaagatc gagcgcgaca    3540
gcgtgcaact ggctccccct gccctgcccg cgccatcggc cgccgtggag cgttcgcgtc    3600
```

```
gtctcgaaca ggaggcggca ggtttggcga agtcgatgac catcgacacg cgaggaacta   3660
tgacgaccaa gaagcgaaaa accgccggcg aggacctggc aaaacaggtc agcgaggcca   3720
agcaggccgc gttgctgaaa cacacgaagc agcagatcaa ggaaatgcag ctttccttgt   3780
tcgatattgc gccgtggccg gacacgatgc gagcgatgcc aaacgacacg gcccgctctg   3840
ccctgttcac cacgcgcaac aagaaaatcc cgcgcgaggc gctgcaaaac aaggtcattt   3900
tccacgtcaa caaggacgtg aagatcacct acaccggcgt cgagctgcgg gccgacgatg   3960
acgaactggt gtggcagcag gtgttggagt acgcgaagcg caccnctatc ggcgagccga   4020
tcaccttcac gttctacgag cttncgcagg acctgggctg gtcgatcaat ggccggtatt   4080
acacgaaggc cgaggaatgc ctgtcgcgcc tacaggcgac ggcgatgggc ttcacgtccg   4140
accgcgttgg gcacctggaa tcggtgtcgc tgctgcaccg cttccgcgtc ctggaccgtg   4200
gcaagaaaac gtcccgttgc caggtcctga tcgacgagga aatcgtcgtg ctgtttgctg   4260
gcgaccacta cacgaaattc atatgggaga agtaccgcaa gctgtcgccg acggcccgac   4320
ggatgttcga ctatttcagc tcgcaccggg agccgtaccc gctcaagctg gaaaccttcc   4380
gcctcatgtg cggatcggat ccacccgcg tgaagaagtg gcgcgagcag gtcggcgaag   4440
cctgcgaaga gttgcgaggc agcggcctgg tggaacacgc ctgggtcaat gatgacctgg   4500
tgcattgcaa acgctagggc cttgtggggt cagttccggc tggggttca gcagccagcg   4560 ctttactggc atttcaggaa caagcgggca ctgctcgacg cacttgcttc gctcagtatc   4620
gctcgggacg cacggcgcgc tctacgaact gccgataaac agaggattaa aattgacaat   4680
tgtgattaag gctcagattc gacggcttgg agcggccgac gtgcaggatt ccgcgagat   4740 ccgattgtcg gccctgaaga aagctccaga gatgttcggg tccgtttacg agcacgagga   4800
gaaaagcccc atggaggcgt tcgctgaacg gttgcgagat gccgtggcat tcggcgccta   4860
catcgacggc gagatcattg ggctgtcggt cttcaaacag gaggacggcc caaggacgc   4920 tcacaaggcg catctgtccg gcgttttcgt ggagcccgaa cagcgaggcc gagggtcgc   4980 cggtatgctg ctgcgggcgt tgccggcggg tttattgctc gtgatgatcg tccgacagat   5040
tccaacggga atcggtgga tgcgcatctt catcctcggc gcacttaata tttcgctatt   5100
ctggagcttg ttgtttattt cggtctaccg cctgccgggc ggggtcgcgg cgacggtagg   5160
cgctgtgcag ccgctgatgg tcgtgttcat ctctgccgct ctgctaggta gcccgatacg   5220
attgatggcg gtcctggggg ctatttgcgg aactgcgggc gtggcgctgt tggtgttgac   5280
accaaacgca gcgctagatc ctgtcggcgt cgcagcgggc ctggcggggg cggtttccat   5340
ggcgttcgga accgtgctga cccgcaagtg gcaacctccc gtgcctctgc tcacctttac   5400
cgcctggcaa ctgcggccg gaggacttct gctcgttcca gtagctttag tgtttgatcc   5460
gccaatcccg atgcctacag gaaccaatgt tctcggcctg gcgtggctcg gcctgatcgg   5520
agcgggttta acctacttcc tttggttccg ggggatctcg cgactcgaac ctacagttgt   5580
ttccttactg ggctttctca gccccagatc tggggtcgat cagccgggga tgcatcaggc   5640
cgacagtcgg aacttcgggt ccccgacctg taccattcgg tgagcaatgg atagggagt   5700 tgatatcgtc aacgttcact tctaaagaaa tagcgccact cagcttcctc agcggcttta   5760
tccagcgatt tcctattatg tcggcatagt tctcaagatc gacagcctgt cacggttaag   5820
cgagaaatga ataagaaggc tgataattcg gatctctgcg agggagatga tatttgatca   5880
caggcagcaa cgctctgtca tcgttacaat caacatgcta ccctccgcga gatcatccgt   5940
```

```
gtttcaaacc cggcagctta gttgccgttc ttccgaatag catcggtaac atgagcaaag   6000
tctgccgcct tacaacggct ctcccgctga cgccgtcccg gactgatggg ctgcctgtat   6060
cgagtggtga ttttgtgccg agctgccggt cggggagctg ttggctggct ggtggcagga   6120
tatattgtgg tgtaaacaaa ttgacgctta gacaacttaa taacacattg cggacgtttt   6180
taatgtactg gggtggtttt tcttttcacc agtgagacgg gcaacagctg attgcccttc   6240
accgcctggc cctgagagag ttgcagcaag cggtccacgc tggtttgccc cagcaggcga   6300
aaatcctgtt tgatggtggt tccgaaatcg gcaaaatccc ttataaatca aagaatagc    6360 ccgagatagg gttgagtgtt gttccagttt ggaacaagag tccactatta agaacgtgg    6420 actccaacgt caaagggcga aaaccgtctc atcagggcga tggcccacta cgtgaaccat   6480
cacccaaatc aagttttttg gggtcgaggt gccgtaaagc actaaatcgg aaccctaaag   6540
ggagcccccg atttagagct tgacggggaa agccggcgaa cgtggcgaga aaggaaggga   6600
agaaagcgaa aggagcgggc gccattcagg ctgcgcaact gttgggaagg gcgatcggtg   6660
cgggcctctt cgctattacg ccagctggcg aaagggggat gtgctgcaag gcgattaagt   6720
tgggtaacgc cagggttttc ccagtcacga cgttgtaaaa cgacggccag tgaattcgag   6780
ctcggtaccc ctactccaaa aatgtcaaag atacagtctc agaagaccaa agggctattg   6840
agacttttca acaaagggta atttcgggaa acctcctcgg attccattgc ccagctatct   6900
gtcacttcat cgaaaggaca gtagaaaagg aaggtggctc ctacaaatgc catcattgcg   6960
ataaaggaaa ggctatcatt caagatgcct ctgccgacag tggtcccaaa gatggacccc   7020
cacccacgag gagcatcgtg gaaaagaag acgttccaac cacgtcttca agcaagtgg    7080 attgatgtga catctccact gacgtaaggg atgacgcaca atcccacccc tactccaaaa   7140
atgtcaaaga tacagtctca gaagaccaaa gggctattga acttttcaa caaagggtaa    7200 tttcgggaaa cctcctcgga ttccattgcc cagctatctg tcacttcatc gaaaggacag   7260
tagaaaagga aggtggctcc tacaaatgcc atcattgcga taaggaaag gctatcattc    7320 aagatgcctc tgccgacagt ggtcccaaag atggaccccc acccacgagg agcatcgtgg   7380
aaaaagaaga cgttccaacc acgtcttcaa agcaagtgga ttgatgtgac atctccactg   7440
acgtaaggga tgacgcacaa tcccactatc cttcgcaaga cccttcctct atataaggaa   7500
gttcatttca tttggagagg acagcccaag cttaaaacaa caatgggata cacaaatgtg   7560 tccatttat taggcctgtt gatggtcttt gttacaccga tggtgttcgc agatcccatg    7620
catcatcatc atcaccaccc catggtgagc aagggcgagg agctgttcac cggggtggtg   7680
cccatcctgg tcgagctgga cggcgacgta aacggccaca gttcagcgt gtccggcgag    7740 ggcgagggcg atgccaccta cggcaagctg accctgaagt tcatctgcac caccggcaag   7800
ctgcccgtgc cctggcccac cctcgtgacc accctgacct acggcgtgca gtgcttcagc   7860
cgctaccccg accacatgaa gcagcacgac ttcttcaagt ccgccatgcc cgaaggctac   7920
gtccaggagc gcaccatctt cttcaaggac gacggcaact acaagacccg cgccgaggtg   7980
aagttcgagg gcgacaccct ggtgaaccgc atcgagctga agggcatcga cttcaaggag   8040
gacggcaaca tcctggggca caagctggag tacaactaca acagccacaa cgtctatatc   8100
atggccgaca agcagaagaa cggcatcaag gtgaacttca agatccgcca caacatcgag   8160
gacggcagcg tgcagctcgc cgaccactac cagcagaaca ccccatcgg cgacggcccc   8220 gtgctgctgc ccgacaacca ctacctgagc acccagtccg ccctgagcaa agaccccaac   8280
gagaagcgcg atcacatggt cctgctggag ttcgtgaccg ccgccgggat cactctcggc   8340
```

```
atggacgagc tgtacaagta aagcggccgc gactctagaa ttcgctgaaa tcaccagtct    8400
ctctctacaa atctatctct ctctattttc tccataaata atgtgtgagt agtttcccga    8460
taagggaaat tagggttctt atagggtttc gctcatgtgt tgagcatata agaaacccett   8520 agtatgtatt tgtatttgta aaatacttct atcaataaaa tttctaattc ctaaaaccaa    8580
aatccagtac taaaatccag atcctctaga gtcgacctgc aggcatgcaa gcttggcgta    8640
atcatggtca tagctgtttc ctgtgtgaaa ttgttatccg ctcacaattc cacacaacat    8700
acgagccgga agcataaagt gtaaagcctg gggtgcctaa tgagtgagct aactcacatt    8760
aattgcgttg cgctcactgc ccgctttcca gtcgggaaac ctgtcgtgcc agctgcatta    8820
atgaatcggc caacgcgcgg ggagaggcgg tttgcgtatt gggccaaaga caaagggcg     8880 acattcaacc gattgaggga gggaaggtaa atattgacgg aaattattca ttaaaggtga    8940
attatcaccg tcaccgactt gagccatttg gaattagag ccagcaaaat caccagtagc     9000
accattacca ttagcaaggc cggaaacgtc accatgaaaa ccatcgatag cagcaccgta    9060
atcagtagcg acagaatcaa gtttgccttt agcgtcagac tgtagcgcgt tttcatcggc    9120
attttcggtc atagccccct tattagcgtt tgccatcttt tcataatcaa atcaccgga     9180 accagagcca ccaccggaac cgcctccctc agagccgcca ccctcagaac cgccaccctc    9240
agagccacca ccctcagagc cgccaccaga accaccacca gagccgccgc cagcattgac    9300
aggaggcccg atctagtaac atagatgaca ccgcgcgcga taatttatcc tagtttgcgc    9360
gctatatttt gttttctatc gcgtattaaa tgtataattg cgggactcta atcataaaaa    9420
cccatctcat aaataacgtc atgcattaca tgttaattat tacatgctta acgtaattca    9480
acagaaatta tatgataatc atcgcaagac cggcaacagg attcaatctt aagaaacttt    9540
attgccaaat gtttgaacga tcggggatca tccgggtctg tggcgggaac tccacgaaaa    9600
tatccgaacg cagcaagata tcgcggtgca tctcggtctt gcctgggcag tcgccgccga    9660
cgccgttgat gtggacgccg ggcccgatca tattgtcgct caggatcgtg gcgttgtgct    9720
tgtcggccgt tgctgtcgta atgatatcgg caccttcgac cgcctgttcc gcagagatcc    9780
cgtgggcgaa gaactccagc atgagatccc cgcgctggag gatcatccag ccggcgtccc    9840
ggaaaacgat tccgaagccc aacctttcat agaaggcggc ggtggaatcg aaatctcgtg    9900
atggcaggtt gggcgtcgct tggtcggtca tttcgaaccc cagagtcccg ctcagaagaa    9960
ctcgtcaaga aggcgataga aggcgatgcg ctgcgaatcg ggagcggcga taccgtaaag   10020
cacgaggaag cggtcagccc attcgccgcc aagctcttca gcaatatcac gggtagccaa   10080
cgctatgtcc tgatagcggt ccgccacacc cagccggcca cagtcgatga atccagaaaa   10140
gcggccattt tccaccatga tattcggcaa gcaggcatcg ccatgggtca cgacgagatc   10200
ctcgccgtcg ggcatgcgcg ccttgagcct ggcgaacagt tcggctggcg cgagcccctg   10260
atgctcttcg tccagatcat cctgatcgac aagaccggct tccatccgag tacgtgctcg   10320
ctcgatgcga tgtttcgctt ggtggtcgaa tgggcaggta gccggatcaa gcgtatgcag   10380
ccgccgcatt gcatcagcca tgatggatac tttctcggca ggagcaaggt gagatgacag   10440
gagatcctgc cccggcactt cgcccaatag cagccagtcc cttcccgctt cagtgacaac   10500
gtcgagcaca gctgcgcaag gaacgcccgt cgtggccagc cacgatagcc gcgctgcctc   10560
gtcctgcagt tcattcaggg caccggacag gtcggtcttg acaaaaagaa ccgggcgccc   10620
ctgcgctgac agccggaaca cggcggcatc agagcagccg attgtctgtt gtgcccagtc   10680
```

-continued

```
atagccgaat agcctctcca cccaagcggc cggagaacct gcgtgcaatc catcttgttc    10740
aatcatgcga aacgatccag atccggtgca gattatttgg attgagagtg aatatgagac    10800
tctaattgga taccgagggg aatttatgga acgtcagtgg agcatttttg acaagaaata    10860
tttgctagct gatagtgacc ttaggcgact tttgaacgcg caataatggt ttctgacgta    10920
tgtgcttagc tcattaaact ccagaaaccc gcggctgagt ggctccttca acgttgcggt    10980
tctgtcagtt ccaaacgtaa aacggcttgt cccgcgtcat cggcggggt cataacgtga    11040 ctcccttaat tctccgctca tgatcagatt gtcgtttccc gccttcagtt taaactatca    11100
gtgtttgaca ggatatattg gcgggtaaac ctaagagaaa agagcgttta ttagaataat    11160
cggatattta aaagggcgtg aaaaggttta ccgttcgtc catttgtatg tgcatgccaa    11220
ccacagggtt ccccagatct ggcgccggcc agcgagacga gcaagattgg ccgccgcccg    11280
aaacgatccg acagcgcgcc cagcacaggt gcgcaggcaa attgcaccaa cgcatacagc    11340
gccagcagaa tgccatagtg ggcggtgacg tcgttcgagt gaaccagatc gcgcaggagg    11400
cccggcagca ccggcataat caggccgatg ccgacagcgt cgagcgcgac agtgctcaga    11460
attacgatca ggggtatgtt gggtttcacg tctggcctcc ggaccagcct ccgctggtcc    11520
gattgaacgc gcggattctt tatcactgat aagttggtgg acatattatg tttatcagtg    11580
ataaagtgtc aagcatgaca aagttgcagc cgaatacagt gatccgtgcc gccctggacc    11640
tgttgaacga ggtcggcgta acggtctga cgacacgcaa actggcggaa cggttggggg    11700
ttcagcagcc ggcgctttac tggcacttca ggaacaagcg ggcgctgctc gacgcactgg    11760
ccgaagccat gctggcggag aatcatacgc attcggtgcc gagagccgac gacgactggc    11820
gctcatttct gatcgggaat gcccgcagct tcaggcaggc gctgctcgcc taccgcgatg    11880
gcgcgcgcat ccatgccggc acgcgaccgg gcgcaccgca gatggaaacg gccgacgcgc    11940
agcttcgctt cctctgcgag gcgggttttt cggccgggga cgccgtcaat gcgctgatga    12000
caatcagcta cttcactgtt ggggccgtgc ttgaggagca ggccggcgac agcgatgccg    12060
gcgagcgcgg cggcaccgtt gaacaggctc cgctctcgcc gctgttgcgg ccgcgataga    12120
acgccttcga cgaagccggt ccggacgcag cgttcgagca gggactcgcg gtgattgtcg    12180
atggattggc gaaaggagg ctcgttgtca ggaacgttga aggaccgaga aagggtgacg    12240
attgatcagg accgctgccg gagcgcaacc cactcactac agcagagcca tgtagacaac    12300
atcccctccc cctttccacc gcgtcagacg cccgtagcag cccgctacgg gcttttcat    12360 gccctgccct agcgtccaag cctcacggcc gcgctcggcc tctctggcgg ccttctggcg    12420
ctcttccgct tcctcgctca ctgactcgct gcgctcggtc gttcggctgc ggcgagcggt    12480
atcagctcac tcaaaggcgg taatacggtt atccacagaa tcaggggata acgcaggaaa    12540
gaacatgtga gcaaaaggcc agcaaaaggc caggaaccgt aaaaaggccg cgttgctggc    12600
gtttttccat aggctccgcc ccctgacga gcatcacaaa aatcgacgct caagtcagag    12660
gtggcgaaac ccgacaggac tataaagata ccaggcgttt ccccctggaa gctccctcgt    12720
gcgctctcct gttccgaccc tgccgcttac cggatacctg tccgcctttc tcccttcggg    12780
aagcgtggcg cttttccgct gcataaccct gcttcggggt cattatagcg attttttcgg    12840
tatatccatc cttttcgca cgatatacag gattttgcca aagggttcgt gtagactttc    12900
cttggtgtat ccaacggcgt cagccggca ggataggtga agtaggccca cccgcgagcg    12960
ggtgttcctt cttcactgtc ccttattcgc acctggcggt gctcaacggg aatcctgctc    13020
tgcgaggctg gccggctacc gccggcgtaa cagatgaggg caagcggatg gctgatgaaa    13080
```

-continued

```
ccaagccaac caggaagggc agcccaccta tcaaggtgta ctgccttcca gacgaacgaa    13140
gagcgattga ggaaaaggcg gcggcggccg gcatgagcct gtcggcctac ctgctggccg    13200
tcggccaggg ctacaaaatc acgggcgtcg tggactatga gcacgtccgc gagctggccc    13260
gcatcaatgg cgacctgggc cgcctgggcg gcctgctgaa actctggctc accgacgacc    13320
cgcgcacggc gcggttcggt gatgccacga tcctcgccct gctggcgaag atcgaagaga    13380
agcaggacga gcttggcaag gtcatgatgg gcgtggtccg cccgagggca gagccatgac    13440 tttttagcc gctaaaacgg ccgggggtg cgcgtgattg ccaagcacgt ccccatgcgc      13500
tccatcaaga agagcgactt cgcggagctg gtgaagtaca tcaccgacga gcaaggcaag    13560
accgagcgcc tttgcgacgc tca                                            13583
```

<210> SEQ ID NO 2
<211> LENGTH: 1215
<212> TYPE: DNA
<213> ORGANISM: artificial sequence
<220> FEATURE:
<223> OTHER INFORMATION: GL-SP

<400> SEQUENCE: 2

```
ccatgggtta tacaaacgtt tcaatcctat taggcttgtt gatggttttc gtcactccta      60
tggtatttgc actcttcggg aagttacacc caggctcccc agaggtaact atgaacatat     120
cacagatgat tacatattgg ggatatccaa atgaggaata tgaagtggtc acggaggacg     180
gatacatttt ggaagtgaac agaataccgt acgggaagaa gaacagtgga aacaccggtc     240
aacgtcccgt cgtgttcctt caacatggac ttctagcaag tgctactaat tggattagca     300
acttgccgaa taactcactt gcctttatct tagcagatgc aggctatgat gtttggctgg     360
gaaacagtag aggcaataca tgggcaaggc gtaatcttta ctactctccg gatagtgttg     420
agttttgggc ttttagcttc gacgaaatgg cgaagtacga tcttccggct actattgact     480
ttatcgttaa gaaaacggga cagaagcagt tacattatgt gggtcattcc caggggacca     540
ctatcggatt catcgccttt tctacgaacc cttccctcgc aaaacgaatc aaaaccttt      600 acgctctcgc gcctgttgca actgtgaaat acacgaagtc tctgattaac aaactgagat     660
ttgttcctca atctttgttc aagtttatct ttggtgataa gattttctat cctcacaact     720
tctttgatca atttcttgcc acagaagttt gctcgcgaga aatgctcaat ctcctatgtt     780
ccaacgcttt gtttatcata tgtggattcg attcgaagaa tttcaatact tctagattgg     840
atgtgtattt gtcacacaat ccagctggga cctctgttca gaatatgttc cattggacac     900
aagctgtgaa aagcggaaag tttcaagctt atgattgggg ttctcccgtc cagaatagga    960
tgcactatga ccagtcacaa cctccttact acaacgtaac agcgatgaac gtgccaattg    1020
ctgtttggaa tggtggtaaa gacctactag ctgatccaca agatgtcggt ctgcttcttc    1080
ctaaacttcc caatttgata taccataaag aaattccatt ctataaccat cttgacttca    1140
tatgggctat ggatgcaccg caagaggtct acaatgatat agtatcgatg attagcgagg    1200
ataagaaatg aattc                                                     1215
```